United States Patent
Windheuser et al.

(10) Patent No.: US 12,171,424 B2
(45) Date of Patent: Dec. 24, 2024

(54) ENDOSCOPE ATTACHMENT MECHANISM FOR USE WITH SUTURE BASED CLOSURE DEVICE

(71) Applicant: BOSTON SCIENTIFIC SCIMED, INC., Maple Grove, MN (US)

(72) Inventors: Kevin Windheuser, Hopkinton, MA (US); Shaun D. Comee, Fiskdale, MA (US); Christopher R. Deuel, Melrose, MA (US); Stan Gilbert, Litchfield, NH (US); Thomas Jones, Milford, MA (US); Briana J. Moretti, Franklin, MA (US); Ashrita Raghuram, Brighton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 136 days.

(21) Appl. No.: 17/671,017

(22) Filed: Feb. 14, 2022

(65) Prior Publication Data
US 2022/0167965 A1 Jun. 2, 2022

Related U.S. Application Data

(63) Continuation of application No. 16/453,744, filed on Jun. 26, 2019, now Pat. No. 11,272,918.
(Continued)

(51) Int. Cl.
*A61B 17/04* (2006.01)
*A61B 1/00* (2006.01)
(Continued)

(52) U.S. Cl.
CPC ........ *A61B 17/0625* (2013.01); *A61B 1/0008* (2013.01); *A61B 17/0469* (2013.01);
(Continued)

(58) Field of Classification Search
CPC ............ A61B 17/0469; A61B 17/0493; A61B 17/06066; A61B 1/00087; A61B 1/00073; A61B 1/012; A61B 1/014; A61B 1/00135
(Continued)

(56) References Cited

U.S. PATENT DOCUMENTS 4,990,038 A * 2/1991 DeLong ............ A61B 17/1664
408/127
5,478,344 A 12/1995 Stone
(Continued)

FOREIGN PATENT DOCUMENTS

CA 2682488 A1 10/2008
DE 202005022017 U1 5/2012
(Continued)

OTHER PUBLICATIONS

International Search Report and Written Opinion dated Aug. 20, 2019 for International Application No. PCT/US2019/033748.
(Continued)

*Primary Examiner* — Tuan V Nguyen
(74) *Attorney, Agent, or Firm* — Seager, Tufte & Wickhem, LLP

(57) ABSTRACT

A suture assembly includes a translation assembly that is axially translatable within a working channel of an endoscope and is adapted to releasably secure and/or release a needle and a distal end cap that is securable to an end of the endoscope and is adapted to releasably secure and/or release the needle in order to pass the needle back and forth between the translation assembly and the distal cap. An attachment mechanism configured to releasably secure the distal endcap to an end of the endoscope.

20 Claims, 51 Drawing Sheets

Related U.S. Application Data

(60) Provisional application No. 62/848,995, filed on May 16, 2019, provisional application No. 62/690,637, filed on Jun. 27, 2018.

(51) Int. Cl.
*A61B 17/06* (2006.01)
*A61B 17/062* (2006.01)

(52) U.S. Cl.
CPC .... *A61B 17/0493* (2013.01); *A61B 17/06066* (2013.01); *A61B 17/0487* (2013.01)

(58) Field of Classification Search
USPC ....... 600/114, 135, 124, 126, 127, 139, 140, 600/141–150
See application file for complete search history.

(56) References Cited

U.S. PATENT DOCUMENTS

| | | |
|---|---|---|
| 5,584,861 A | 12/1996 | Swain et al. |
| 6,059,719 A * | 5/2000 | Yamamoto ....... A61B 17/00234 606/1 |
| 6,086,608 A | 7/2000 | Ek et al. |
| 6,200,329 B1 | 3/2001 | Fung et al. |
| 6,494,888 B1 | 12/2002 | Laufer et al. |
| 6,506,196 B1 | 1/2003 | Laufer |
| 6,554,845 B1 | 4/2003 | Fleenor et al. |
| 6,569,085 B2 | 5/2003 | Kortenbach et al. |
| 6,626,917 B1 | 9/2003 | Craig |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,189,247 B1 | 3/2007 | Zirps et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 8,057,494 B2 | 11/2011 | Laufer et al. |
| 8,062,314 B2 | 11/2011 | Sixto, Jr. et al. |
| 8,066,721 B2 | 11/2011 | Kortenbach et al. |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale |
| 8,425,555 B2 | 4/2013 | Page et al. |
| 8,454,631 B2 | 6/2013 | Viola et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,585,720 B2 | 11/2013 | Gross et al. |
| 8,632,553 B2 | 1/2014 | Sakamoto et al. |
| 8,679,136 B2 | 3/2014 | Mitelberg |
| 8,709,022 B2 | 4/2014 | Stone et al. |
| 8,764,771 B2 | 7/2014 | Chu |
| 8,882,785 B2 | 11/2014 | DiCesare et al. |
| 8,926,634 B2 | 1/2015 | Rothe et al. |
| 8,992,570 B2 | 3/2015 | Gambale et al. |
| 9,011,466 B2 | 4/2015 | Adams et al. |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,320,515 B2 | 4/2016 | Dana et al. |
| 9,486,126 B2 | 11/2016 | West et al. |
| 9,504,465 B2 | 11/2016 | Chu |
| 9,510,817 B2 | 11/2016 | Saadat et al. |
| 9,549,728 B2 | 1/2017 | Chu |
| 9,750,494 B2 | 9/2017 | Gross et al. |
| 9,788,831 B2 | 10/2017 | Mitelberg |
| 9,844,366 B2 | 12/2017 | Woodard, Jr. et al. |
| 9,867,610 B2 | 1/2018 | Mitelberg et al. |
| 10,045,871 B2 | 8/2018 | Saadat et al. |
| 10,143,463 B2 | 12/2018 | Dana et al. |
| 10,194,902 B2 | 2/2019 | Nobles et al. |
| 10,335,142 B2 | 7/2019 | Raybin et al. |
| 2002/0107530 A1 | 8/2002 | Sauer et al. |
| 2002/0116011 A1* | 8/2002 | Chee Chung ...... A61B 17/0469 606/145 |
| 2003/0195529 A1 | 10/2003 | Takamoto et al. |
| 2003/0204205 A1 | 10/2003 | Sauer et al. |
| 2004/0002699 A1 | 1/2004 | Ryan et al. |
| 2004/0138706 A1 | 7/2004 | Abrams et al. |
| 2005/0033319 A1 | 2/2005 | Gambale et al. |
| 2005/0250985 A1 | 11/2005 | Saadat et al. |
| 2006/0282094 A1 | 12/2006 | Stokes et al. |
| 2007/0270908 A1 | 11/2007 | Stokes et al. |
| 2008/0086148 A1 | 4/2008 | Baker et al. |
| 2008/0108874 A1* | 5/2008 | Waller ............ A61B 17/12013 606/140 |
| 2009/0177031 A1 | 7/2009 | Surti et al. |
| 2009/0282091 A1 | 11/2009 | Komori |
| 2010/0137681 A1 | 6/2010 | Ewers et al. |
| 2010/0198006 A1 | 8/2010 | Greenburg et al. |
| 2012/0158023 A1 | 6/2012 | Miltelberg et al. |
| 2012/0259175 A1 | 10/2012 | Reydel et al. |
| 2012/0271327 A1 | 10/2012 | West et al. |
| 2013/0096581 A1 | 4/2013 | Gilkey et al. |
| 2013/0304093 A1 | 11/2013 | Serina et al. |
| 2014/0121457 A1 | 5/2014 | Mori et al. |
| 2014/0128668 A1 | 5/2014 | Cox et al. |
| 2015/0126983 A1 | 5/2015 | Alvarado et al. |
| 2016/0045197 A1 | 2/2016 | Mitelberg et al. |
| 2017/0042534 A1 | 2/2017 | Nobles et al. |
| 2017/0086817 A1 | 3/2017 | Mitelberg |
| 2017/0086818 A1 | 3/2017 | Mitelberg |
| 2017/0119371 A1 | 5/2017 | Mims et al. |
| 2017/0319197 A1 | 11/2017 | Gross et al. |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |

(56) References Cited

U.S. PATENT DOCUMENTS

| | | |
|---|---|---|
| 2018/0221009 A1 | 8/2018 | Mitelberg et al. |
| 2018/0235604 A1 | 8/2018 | Comee et al. |
| 2018/0344501 A1 | 12/2018 | Saadat et al. |

FOREIGN PATENT DOCUMENTS

| | | | |
|---|---|---|---|
| EP | 1520509 | A1 | 4/2005 |
| EP | 2108304 | A2 | 10/2009 |
| JP | 2000014633 | A | 1/2000 |
| JP | 2002000545 | A | 1/2002 |
| JP | 2009545376 | A | 12/2009 |
| JP | 2021259040 | A | 10/2021 |
| WO | 0189393 | A1 | 11/2001 |
| WO | 2008016592 | A2 | 2/2008 |
| WO | 2008045376 | A2 | 4/2008 |
| WO | 2008098124 | A1 | 8/2008 |
| WO | 2010036227 | A1 | 4/2010 |
| WO | 2017087856 | A1 | 5/2017 |
| WO | 2018156603 | A1 | 8/2018 |
| WO | 2020006122 | A1 | 1/2020 |

OTHER PUBLICATIONS

International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
International Search Report and Written Opinion dated Sep. 20, 2019 for International Application No. PCT/US2019/049774.
International Search Report and Written Opinion dated Nov. 18, 2019 for International Application No. PCT/US2019/0393312.

* cited by examiner

ENDOSCOPE ATTACHMENT MECHANISM FOR USE WITH SUTURE BASED CLOSURE DEVICE

CROSS-REFERENCE TO RELATED APPLICATIONS

This application is a continuation of U.S. patent application Ser. No. 16/453,744, filed Jun. 26, 2019, which claims the benefit of priority under 35 U.S.C. § 119 of U.S. Provisional Application No. 62/848,995 filed May 16, 2019 and U.S. Provisional Application No. 62/690,637, filed Jun. 27, 2018, the entire disclosures of which are hereby incorporated by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for known closure methods. Examples of such endoscopic treatments include removal of large lesions, tunneling under the mucosal layer, full thickness removal of tissue, treating other organs by passing outside of the gastrointestinal tract, and post-surgical repair of post-surgical leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. An example is a suture assembly for use in combination with an endoscope having a working channel and a distal end. The suture assembly includes a translation assembly that is axially translatable within the working channel and that includes a needle configured to carry a suture, a distal shuttle configured to releasably secure the needle and a sleeve that is disposable over the distal shuttle. The sleeve is movable between a locked position in which the needle is secured to the distal shuttle and an unlocked position in which the needle is releasable from the distal shuttle. A distal endcap is securable to the distal end of the endoscope and is configured to engage the needle when the needle is advanced distally into the endcap and to release the needle when the needle is locked to the distal shuttle and the distal shuttle is withdrawn proximally. An attachment mechanism is disposable over an exterior of the endoscope proximate the distal end thereof and is configured to releasably secure the distal endcap relative to the distal end of the endoscope.

Alternatively or additionally, the attachment mechanism may include an inner collet member that is configured to engage the distal endcap and form a compressive fit with the endoscope and an outer collet member that is configured to engage the inner collet member in order to form the compressive fit between the inner collet member and the endoscope.

Alternatively or additionally, the distal endcap may further include an annular flange disposed at a proximal end of the distal endcap, and the inner collet member may further include a corresponding annular slot disposed near a distal end of the inner collet member, the annular slot configured to engage the annular flange, thereby providing an interference fit between the distal endcap and the inner collet member.

Alternatively or additionally, the inner collet member may include an body having a plurality of fingers extending axially in a proximal direction from the distal end of the inner collet member, the plurality of fingers defining an inner surface that is configured to engage the endoscope and an outer surface that provides threads to threadedly engage the outer collet adaptor.

Alternatively or additionally, the outer collet member may be configured to urge the plurality of fingers inwardly as the outer collet member is advanced over the inner collet member.

Alternatively or additionally, the attachment mechanism may include a split ring attachment mechanism disposable over an exterior of the endoscope proximate the distal end thereof, the split ring attachment mechanism including an endoscope engaging portion adapted to engage the endoscope in a compressive fit and a distal endcap engaging portion adapted to engage the distal endcap in an interference fit.

Alternatively or additionally, the split ring attachment mechanism may include an elongate body having an inner surface that is adapted to fit over an exterior surface of the endoscope and a living hinge extending longitudinally along the elongate body. The elongate body includes a first body portion extending circumferentially in a first direction from the living hinge and a second body portion extending circumferentially in a second direction from the living hinge.

Alternatively or additionally, once the elongate body has been advanced radially over the endoscope and the distal end cap, the elongate body may be configured to be held in a locking configuration in which the distal endcap is secured to the distal end of the endoscope via one or more members that extend at least partially radially around the elongate body.

Alternatively or additionally, the distal endcap may further include an annular flange disposed at a proximal end of the distal endcap, and the split ring attachment mechanism may further include a corresponding annular slot configured to engage the annular flange, thereby providing an interference fit between the distal endcap and the split ring attachment mechanism.

Alternatively or additionally, the inner collet member may be integrally formed with the distal endcap.

Alternatively or additionally, the inner collet member may include a plurality of fingers extending proximally from the distal endcap, and the outer collet member may include a ring that is configured to be moved proximally over the plurality of fingers, thereby pressing the plurality of fingers into a compressive fit with the endoscope.

Alternatively or additionally, the attachment mechanism may include a fixation member extending from the distal endcap and an elastomeric sleeve configured to form a compressive fit with the endoscope, the elastomer sleeve including a fixation aperture that is complementary to the fixation member.

Another example is a suture assembly for use in combination with an endoscope having a working channel and a distal end. The suture assembly includes a translation assembly that is axially translatable within the working channel and is adapted to releasably engage and disengage a needle. A distal endcap is securable to the distal end of the endoscope and is adapted to releasable engage the needle when the translation assembly disengages the needle and to disengage the needle when the translation assembly engages the needle, the distal endcap including a fixation flange disposed near a proximal end of the distal endcap. An inner collet member is configured to engage the distal endcap and form a compressive fit with the endoscope and an outer collet member is configured to engage the inner collet member in order to form the compressive fit between the inner collet member and the endoscope.

Alternatively or additionally, the outer collet member may be threadedly engageable with the inner collet member in order to form the compressive fit with the endoscope.

Alternatively or additionally, the distal endcap may further include an annular flange disposed at a proximal end of the distal endcap, and the inner collet member may further include a corresponding annular slot disposed near a distal end of the inner collet member, the annular slot configured to engage the annular flange, thereby providing an interference fit between the distal endcap and the inner collet member.

Alternatively or additionally, the inner collet member may include an body having a plurality of fingers extending axially in a proximal direction from the distal end of the inner collet member, the plurality of fingers defining an inner surface that is configured to engage the endoscope and an outer surface that provides threads to threadedly engage the outer collet adaptor.

Alternatively or additionally, the outer collet member may be configured to urge the plurality of fingers inwardly as the outer collet member is advanced over the inner collet member.

Another example is a suture assembly for use in combination with an endoscope having a working channel and a distal end. The suture assembly includes a translation assembly that is axially translatable within the working channel and is adapted to releasably engage and disengage a needle. A distal endcap is securable to the distal end of the endoscope and is adapted to releasable engage the needle when the translation assembly disengages the needle and to disengage the needle when the translation assembly engages the needle, the distal endcap including a fixation flange disposed near a proximal end of the distal endcap. A split ring device is disposable over an exterior of the endoscope proximate the distal end thereof, the split ring device including a cylindrical inner surface adapted to frictionally engage an outer surface of the endoscope and an annular slot adapted to engage the fixation flange in an interference fit.

Alternatively or additionally, the split ring device may include an inner surface that is adapted to fit over an exterior surface of the endoscope.

Alternatively or additionally, the split ring device may include a living hinge that divides the split ring device into a first clamping portion extending circumferentially in a first direction from the living hinge and a second clamping portion extending circumferentially in a second direction from the living hinge.

Alternatively or additionally, the split ring device may be movable between a locking configuration in which the first clamping portion and the second clamping portion frictionally engage an outer surface of the endoscope and an engagement configuration in which the first clamping portion and the second clamping portion are deflected away from the locking configuration.

Alternatively or additionally, the split ring device may further include a first hook extending from the first clamping portion and a second hook extending from the second body clamping portion.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
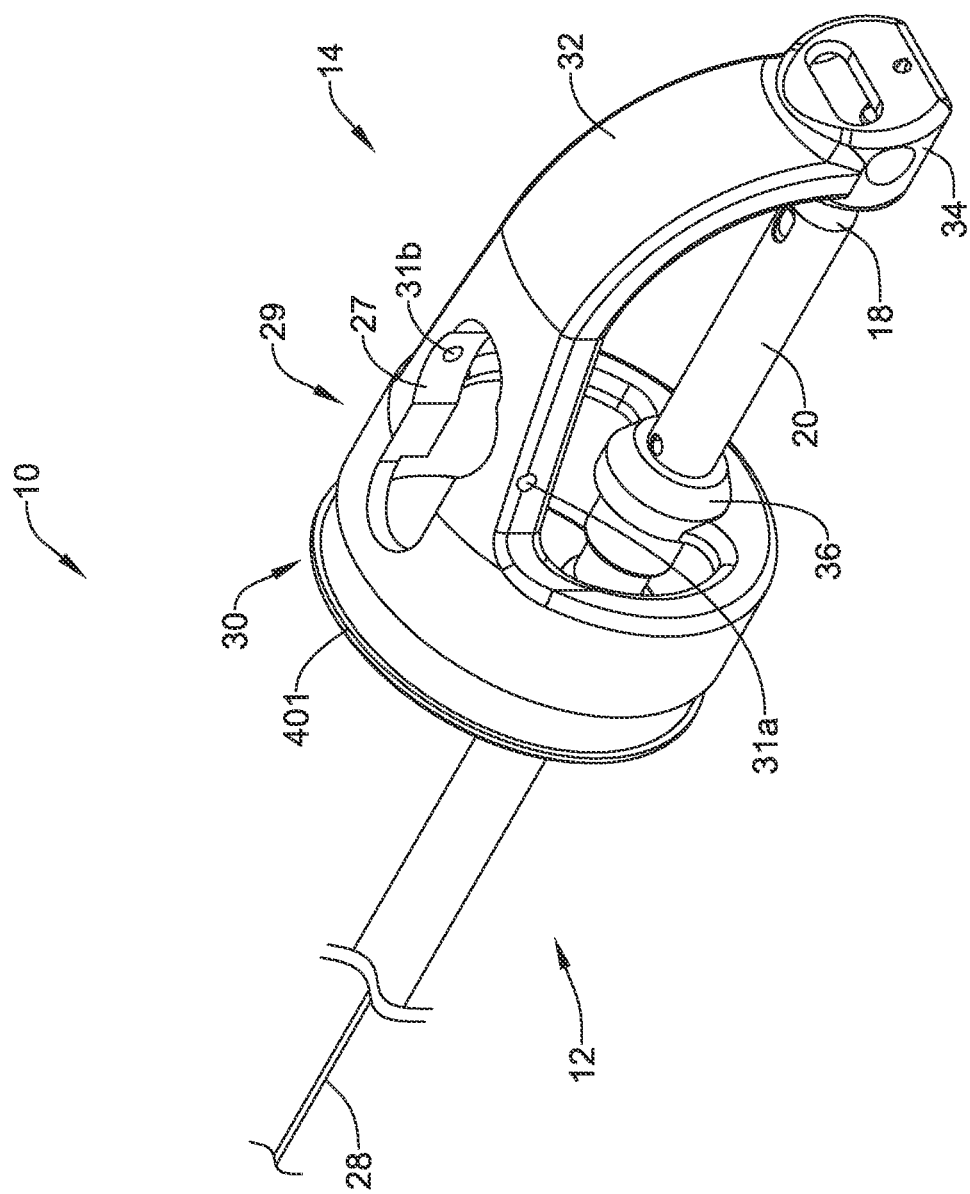
FIG. 1 is a perspective view of an illustrative suture device in accordance with an example of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used within a single working or available channel of an endoscope, and in some embodiments may be operated by a single individual, although in some embodiments a second individual may be involved. In some embodiments, the suture devices described herein may be considered as operating along a single line of operation. The device itself may be translatable distally and proximally within a working channel, and a handle portion may itself be translatable distally and proximally along the same line of operation in locking and unlocking a needle to be able to pass the needle back and forth between an active portion of the suture device and a passive portion of the suture device. The device may be configured to enable the needle to be selectively locked into either of a more distal position or a more proximal position, and the device may itself be translated distally or proximally with the needle locked in place in order to move the needle, and hence a suture, relative to the tissue being repaired.

FIG. 1 is a perspective view of a suture device 10 that may be considered as being configured for use in combination with a delivery system including a lumen that extends through the delivery system. For example, the delivery system may be an endoscope having a working channel. The delivery system may also be a catheter. It will be appreciated that there is a change in scale on either side of the break line shown. In some embodiments, the suture device 10 may be considered as including a suture translation assembly 12 that is configured to be axially translatable within the lumen of the delivery system and a distal assembly 14 that is configured to be secured to a distal end of the delivery system. The suture translation assembly 12 extends into the distal assembly 14 and includes a needle 16 that may be used to carry a suture as well as a distal shuttle 18 that is configured to releasably secure the needle 16.

A member 20 may be disposed over the distal shuttle 18 and, as will be shown in subsequent Figures, is movable between a locked position in which the needle 16 is secured to the distal shuttle 18 and an unlocked position in which the needle 16 is releasable from the distal shuttle 18. In some embodiments, for example, the member 20 may be a sleeve 20. A user interface may extend proximally from the distal shuttle 18 and the sleeve 20, and may be configured to move the sleeve 20 between the locked position and the unlocked position. A shaft 28 may extend distally to the suture translation assembly 12, and may in particular be coupled to the sleeve 20. The user interface may take a number of different forms. For examples, the user interface may be the user interface 22 as described and illustrated in U.S. Patent Application Publication No. 2018/0235604, which publication is incorporated by reference herein in its entirety. In some embodiments, the user interface may be as described in a provisional application Ser. No. 62/794,075 filed Jan. 18, 2019 and entitled ENDOSCOPIC SUTURING CONTROL HANDLE, which application is incorporated by reference herein in its entirety. In some instances, the user interface may be as described in a provisional application filed on the even date herewith, entitled CONTROL HANDLE FOR ENDOSCOPIC SUTURING, which application is incorporated by reference herein in its entirety. These are just examples.

In some embodiments, the distal assembly 14 includes a body 29 having a proximal connector 30 that may be configured to be coupled to the distal end of an endoscope or other delivery system. In some embodiments, as illustrated, the proximal connector 30 may include a fixation feature 401. As will be discussed with respect to subsequent Figures, the fixation feature 401, which may in some embodiments be considered as being a fixation flange 401, helps to secure the distal assembly 14 to the distal end of an endoscope or other delivery system using a split ring attachment mechanism.

The body 29 includes an arm 32 that extends to an endcap 34. As will be discussed, the endcap 34 may be configured to releasably engage and disengage the needle 16. In some embodiments, for example, the endcap 34 may be configured to engage the needle 16 when the needle 16 is advanced distally into the endcap 34, and to release the needle 16 when the needle 16 is locked into the distal shuttle 18 (as will be discussed) and the distal shuttle 18 is withdrawn proximally. The distal assembly 14 may be considered as including a guide member 36 that may be secured to or integrally formed with the body 29, and may permit the suture translation assembly 12 to extend through the guide member 36 and to translate relative to the guide member 36. In some embodiments, the body 29 may include an aperture 27 that may enable other devices to be inserted through the aperture 27. In some instances, as will be discussed with respect to subsequent Figures, the aperture 27 may be configured to accommodate a side-saddled lumen attachment element. In some embodiments, the aperture 27 may include one or more of a pin aperture 31a and a pin aperture 31b that may, for example, be used to mount the aforementioned side-saddled lumen attachment element, or possibly other features as well.

Figure 2:
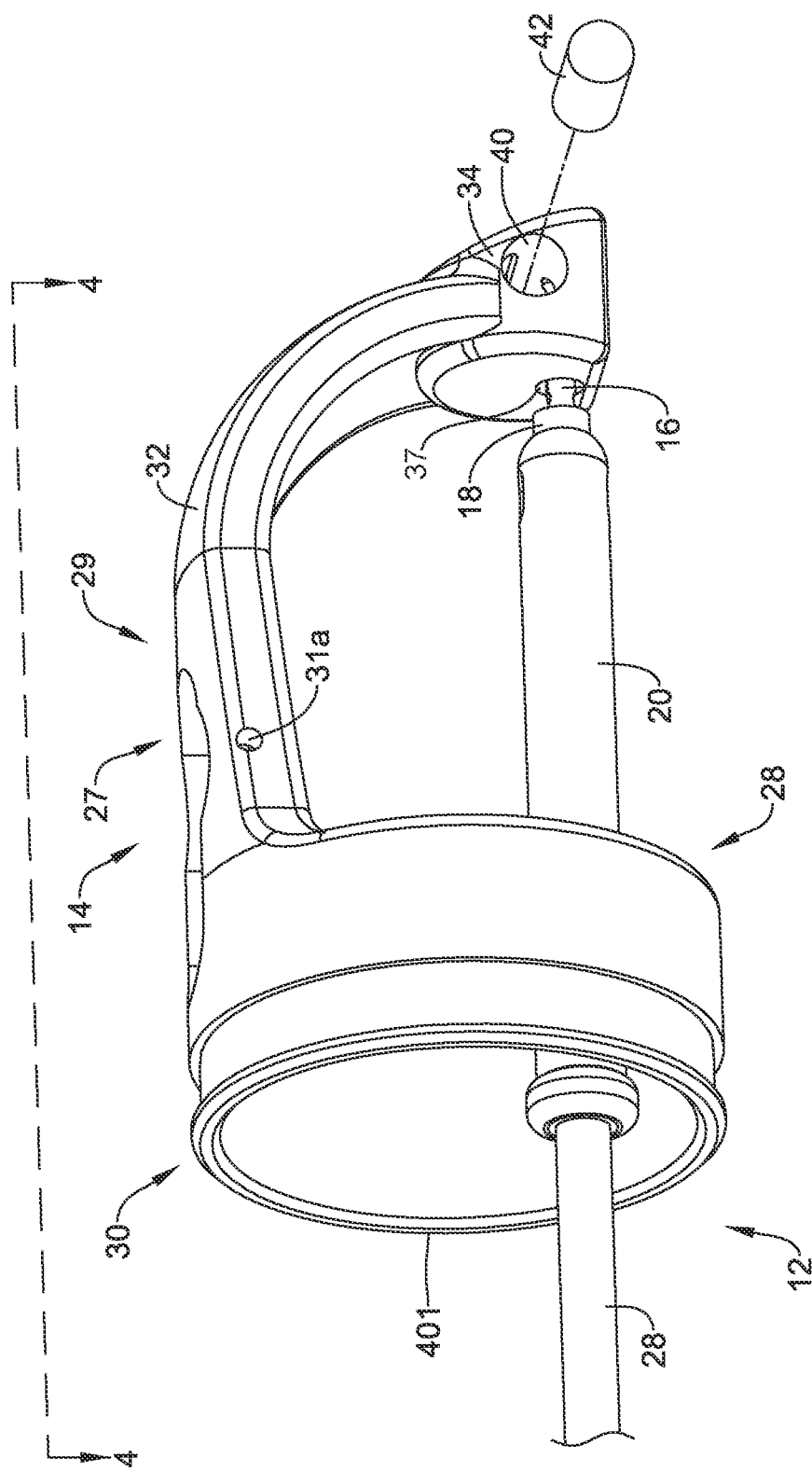
FIG. 2 is a perspective view of a distal assembly forming part of the illustrative suture device of FIG. 1, shown in an extended position.
Figure 3:
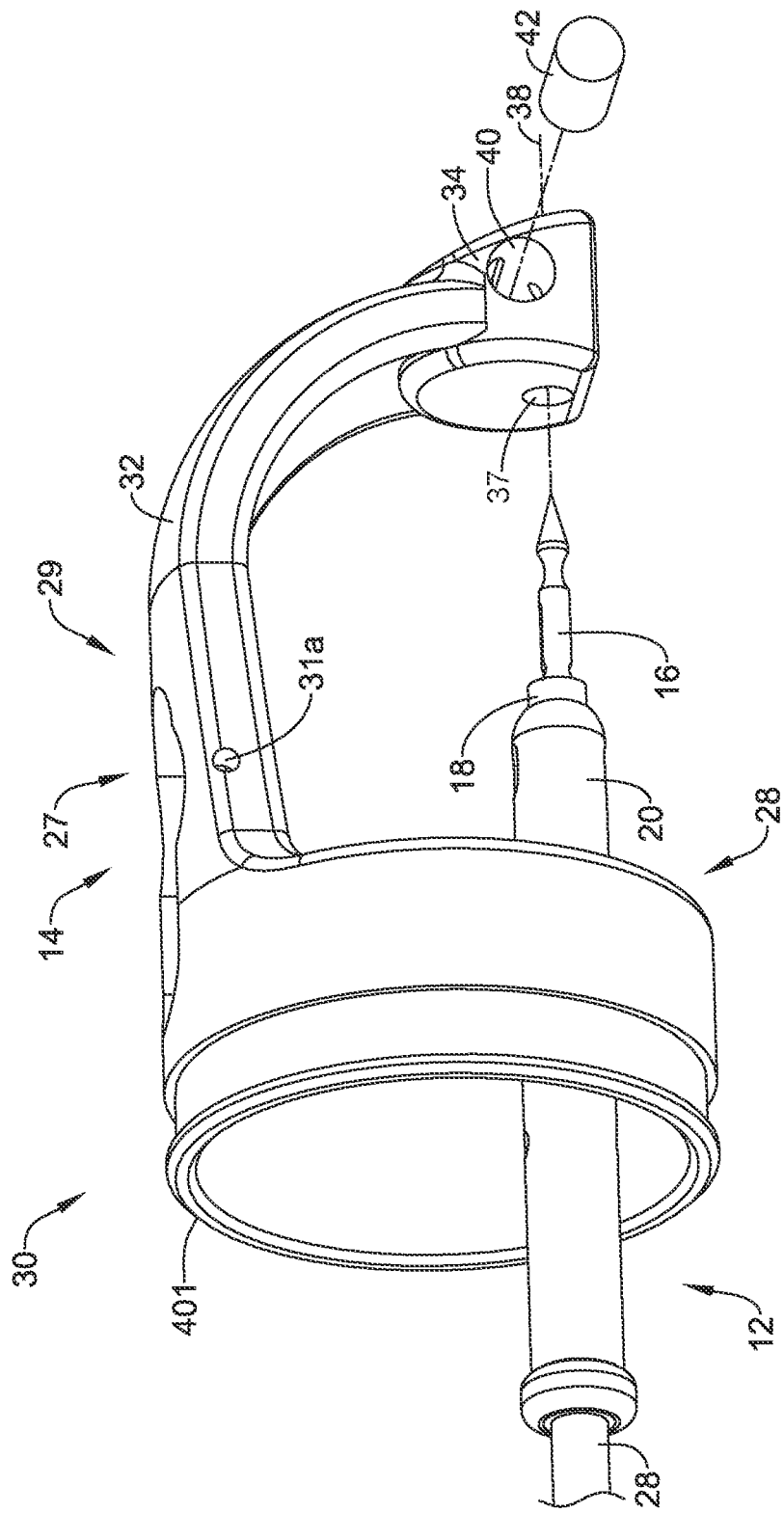
FIG. 3 is a perspective view of the distal assembly of FIG. 2, shown in a retracted position.

FIG. 2 and FIG. 3 show the suture translation assembly 12 extended through the guide member 36 and into the distal assembly 14. In FIG. 2, the suture translation assembly 12 is shown in an extended position in which the needle 16 extends into the endcap 34 while in FIG. 3, the suture translation assembly 12 is shown in a retracted position in which the needle 16 has been withdrawn proximally from the endcap 34. In some embodiments, as can be seen, the endcap 34 includes a proximal needle opening 37 that is configured to help guide the needle 16 into the proximal needle opening 37 as well as to accommodate the needle 16 when the needle 16 is advanced distally into the endcap 34. In some embodiments, the proximal needle opening 37 may extend all the way through the endcap 34 while in other cases the proximal needle opening 37 may not pass all the way through the endcap 34. In some instances, as shown, the proximal needle opening 37 may be considered as being aligned with a longitudinal axis 38 of the needle 16 (as shown in FIG. 3).

One or more securement openings 40 may be arranged orthogonal to the proximal needle opening 37 and one or more securements 42 that are configured to be disposed within the one or more securement openings 40, and which are configured to releasably engage the distal detent (as will be discussed) of the needle 16. In some embodiments, there may be a pair of securement openings 40, one on either side of the endcap 34. In some embodiments, there may be a pair of securements 42, with one disposed within each of the pair of securement openings 40. In some embodiments, while shown schematically, the one or more securements 42 may be springs or coils, for example.

Figure 4:
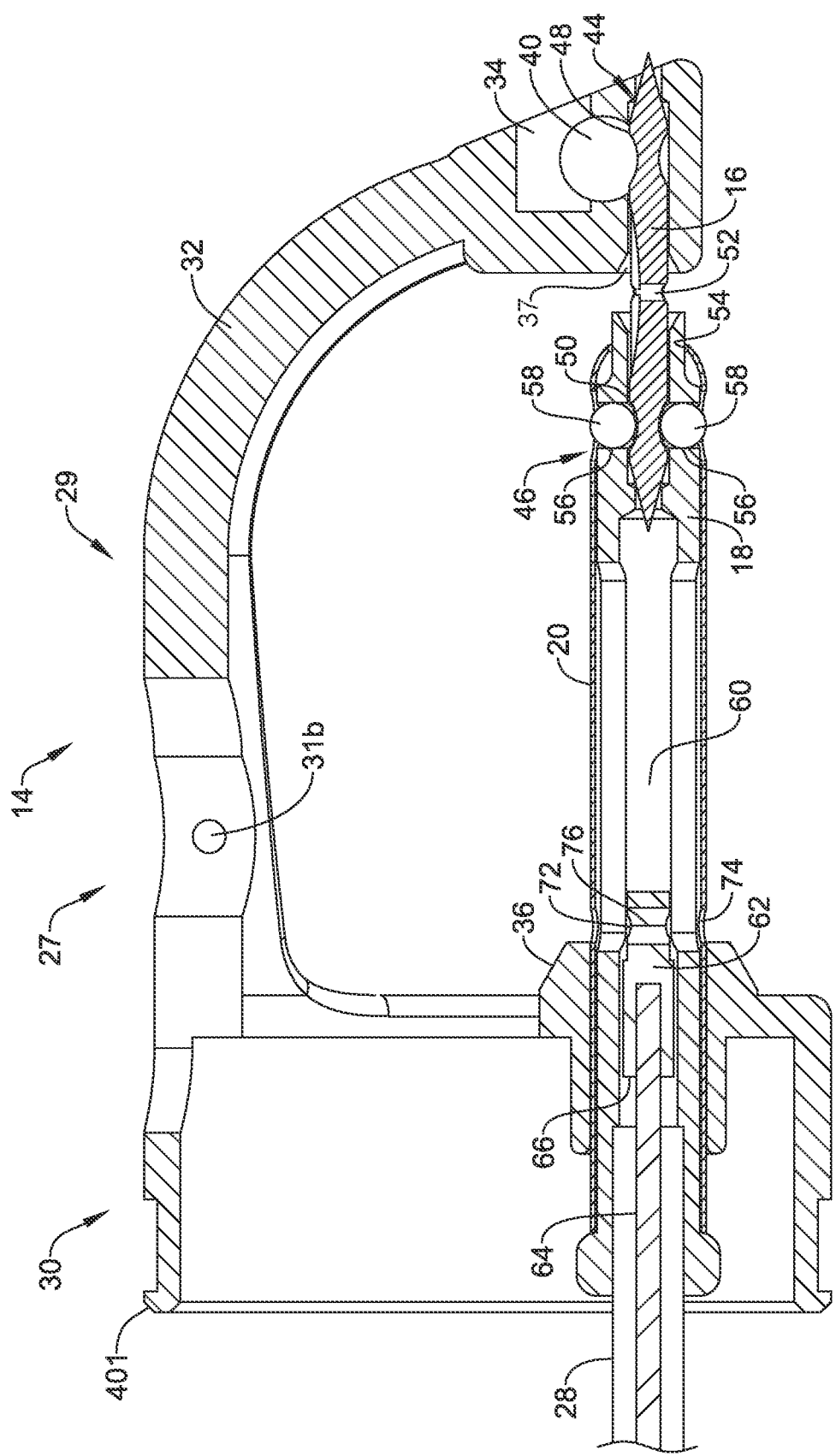
FIG. 4 is a cross-sectional view of the distal assembly of FIG. 2, taken along the line 4-4.
Figure 5:
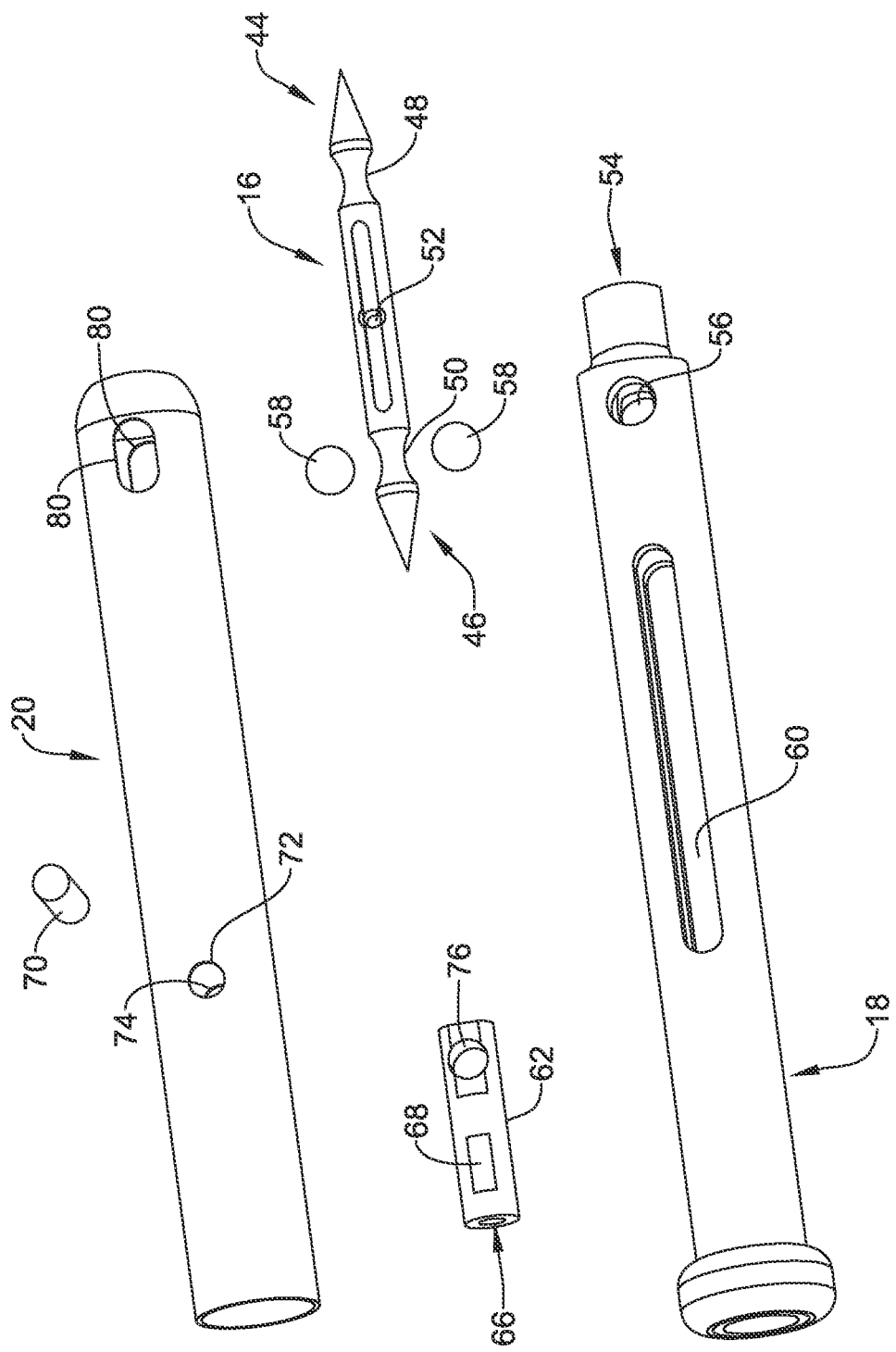
FIG. 5 is an exploded view of a portion of a suture translation assembly forming part of the illustrative suture device of FIG. 1.

FIG. 4 is a cross-sectional view of the distal assembly 14, with the suture translation assembly 12 disposed within the distal assembly 14. FIG. 5 is an exploded view of the suture translation assembly 12. The needle 16 may be considered as including a distal region 44 and a proximal region 46. In some embodiments, the distal region 44 may include a distal detent 48 for releasably engaging the endcap 34 and the proximal region 46 may include a proximal detent 50 for releasably engaging the distal shuttle 18. The needle 16 may, as shown, include an aperture 52 for accommodating a suture line passing therethrough.

In some embodiments, the distal shuttle 18 may be considered as including a distal needle opening 54 that is configured to accommodate the needle 16 when the distal shuttle 18 is advanced distally over the needle 16 and that is aligned with the longitudinal axis 38 of the needle 16. One or more bearing ball openings 56 may be arranged orthogonal to the distal needle opening 54 such that the one or more bearing ball openings 56 align with the proximal detent 50 when the needle 16 is secured to the distal shuttle 18. In some embodiments, one or more bearing balls 58 may be disposed within the one or more bearing ball openings 56 and may be configured to be disposed within the proximal detent 50 when the needle is secured to the distal shuttle 18.

In some embodiments, the distal shuttle 18 includes an internal void 60 and a sleeve capture member 62 that is slidingly disposed within the internal void 60. In some embodiments, the sleeve capture member 62 may be coupled to a cable 64 extending distally within the shaft 28 and into a cable aperture 66 and secured via a crimp or other mechanical connection 68. In some embodiments, the sleeve capture member 62 may be coupled to the sleeve 20 via a pin 70 that extends through first and second sleeve connection apertures 72, 74 and a corresponding aperture 76 extending through the sleeve capture member 62 as well as extending through the internal void 60.

Figure 6:
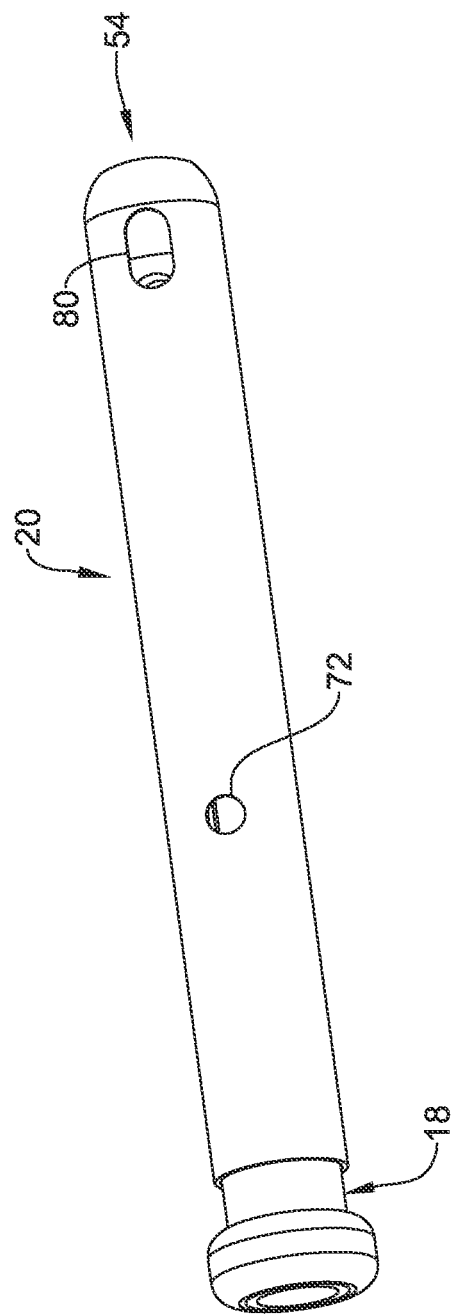
FIG. 6 is a side view of a distal shuttle and a member forming part of the suture translation assembly, with the member shown extended in a locked position.

In some embodiments, the sleeve 20 includes one or more sleeve openings 80 that may be smaller in diameter, or smaller in width, than the diameter of the one or more bearing balls 58. In some embodiments, the sleeve 20 may include a pair of sleeve openings 80, corresponding to a pair of bearing ball openings 56 and a pair of bearing balls 58. When the sleeve 20 is in the locked position, as shown for example in FIG. 6, the one or more sleeve openings 80 are misaligned with, or do not align with, the one or more bearing ball openings 56, and so the one or more bearing balls 58 engage the proximal detent 50 of the needle 16. The sleeve 20 prevents the one or more bearing balls 58 from being pushed out of the proximal detent 50.

Figure 7:
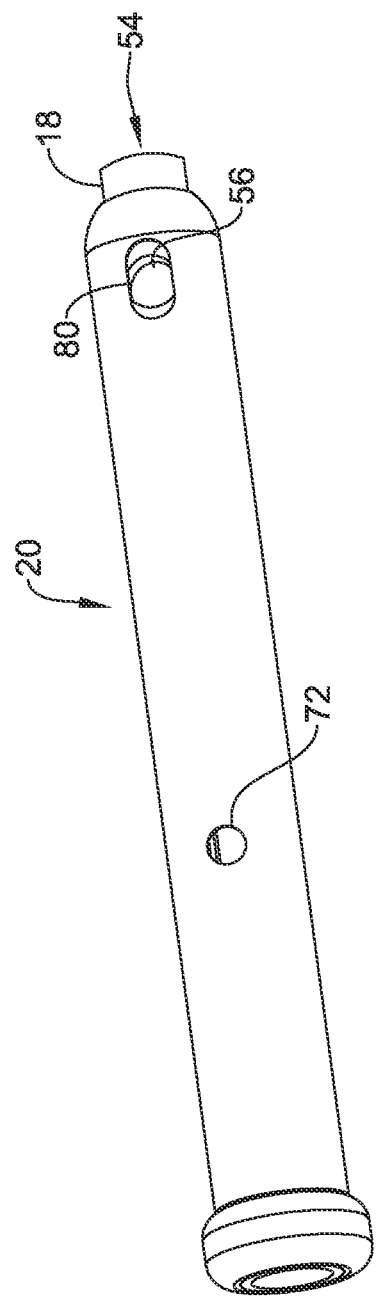
FIG. 7 is a side view of the distal shuttle and the member of FIG. 6, with the member shown retracted in an unlocked position.

Conversely, when the sleeve 20 is in the unlocked position, as shown for example in FIG. 7, the one or more sleeve openings 80 are aligned with the one or more bearing ball openings 56. This permits the one or more bearing balls 58 to move radially out, into the one or more sleeve openings 80, a distance sufficient to permit the one or more bearing balls 58 to clear the proximal detent 50 of the needle 16 in response to a force applied to the one or more bearing balls 58 by the needle 16. With reference to FIG. 4, while the suture translation assembly 12 is shown advanced into the distal assembly 14, the sleeve 20 is in the unlocked position relative to the distal shuttle 18, and thus the one or more bearing balls 58 may be seen as extending partially into the one or more sleeve openings 80.

In some embodiments, it will be appreciated that the distal shuttle 18, and the sleeve 20, in combination, provide an active connection to the needle 16 while the distal endcap 34 provides a passive connection to the needle 16. If the needle 16 is moved distally into the distal endcap 34, the distal endcap 34 will grab onto the needle 16, with the one or more securements 42 engaging the distal detent 48. If the needle 16 is subsequently moved proximally, the axial force applied overcomes any resistance provided by the one or more securements 42, and the needle 16 is able to release from the distal endcap 34 and move proximally. In contrast, the active connection to the needle 16 provided by the distal shuttle 18 and the sleeve 20, however, requires action to move the sleeve 20, relative to the distal shuttle 18, between the locked position and the unlocked position. The user interface provides a mechanism for positively moving the sleeve 20 between the locked and unlocked positions.

Figure 8:
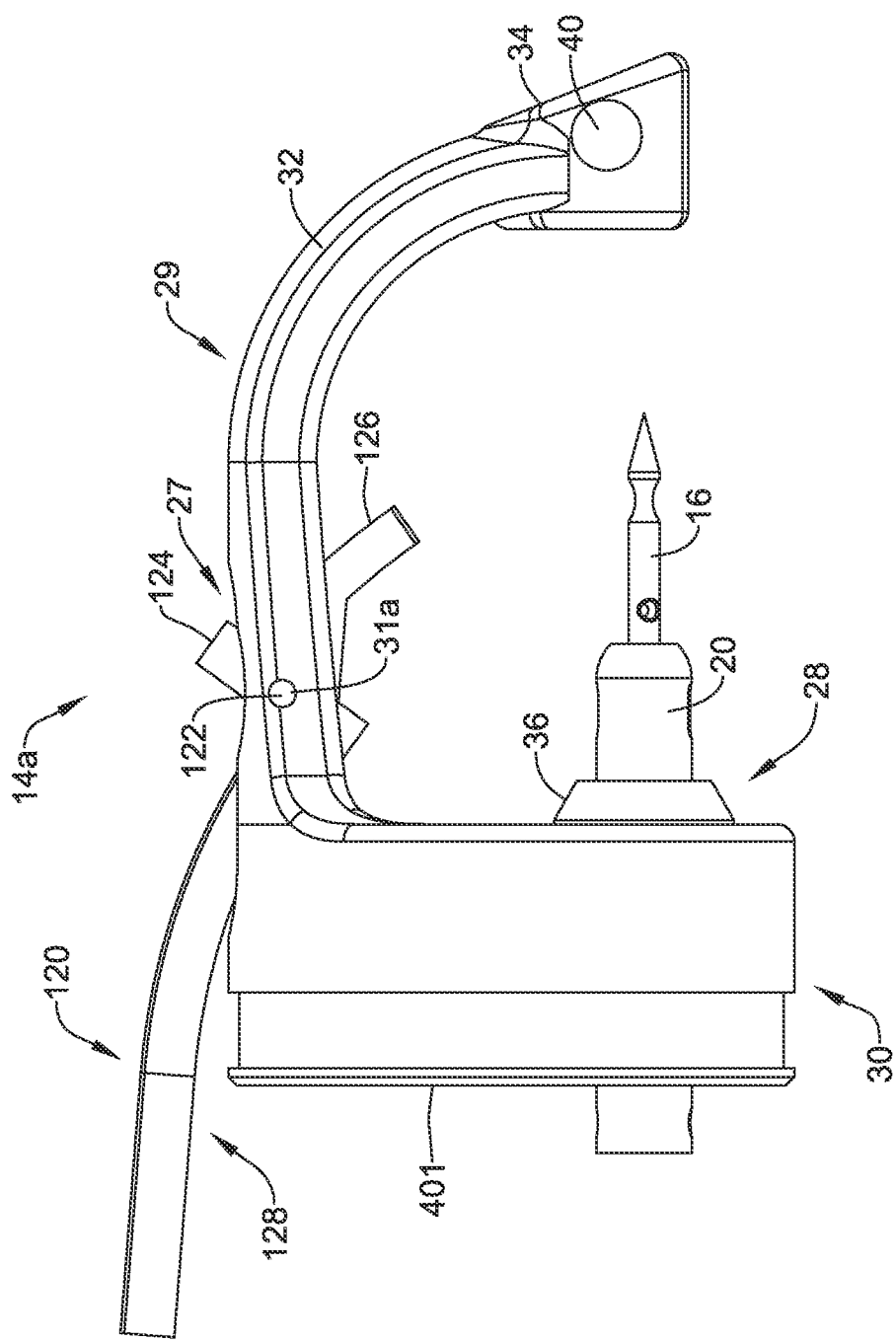
FIG. 8 is a side view of a distal assembly usable in the suture device of FIG. 1 in accordance with an example of the disclosure.

FIG. 8 is a side view of a distal assembly 14a that may, for example, be usable in the suture device 10 shown in FIG. 1. The distal assembly 14a is similar to the distal assembly 14 shown in previous Figures, but includes a side-saddled lumen attachment element 120 that is coupled to the body 29 of the distal assembly 14a. In some embodiments, the side-saddled lumen attachment element 120 may include one or two pegs 122 that fit into the pin apertures 31a and 31b (pin aperture 31a is visible in this view) and thus enable the side-saddled lumen attachment element 120 to pivot relative to the body 29 of the distal assembly 14a. In some embodiments, the side-saddled lumen attachment element 120 includes a ring 124, from which the pegs 122 extend, a distal region 126 and a body 128 that in some instances has a curvature to it.

Figure 9:
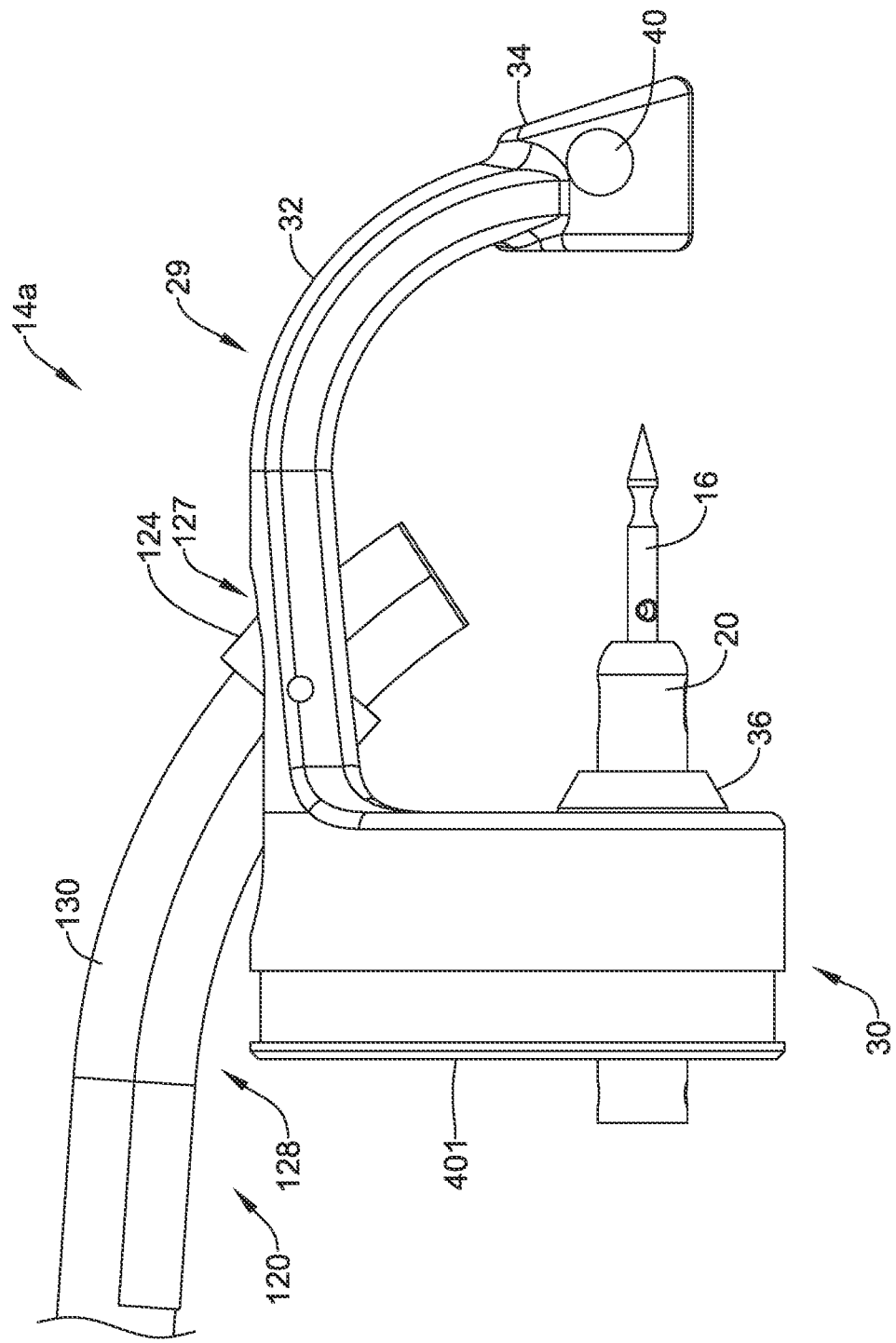
FIG. 9 is a side view of the distal assembly of FIG. 8 in combination with an attached flexible lumen.

In some embodiments, the distal region 126 and the body 128 have a semi-circular profile in order to accommodate a lumen such as a flexible lumen 130 that may engage within the side-saddled lumen attachment element 120 via a frictional or compressive fit as shown in FIG. 9. The flexible lumen 130 may be polymeric or metallic. A polymeric lumen may, for example, be expanded to a full working dimension by extending a mandrel through the flexible lumen 130 after the flexible lumen 130 has been placed relative to the side-saddled lumen attachment element 120.

In some embodiments, the side-saddled attachment element 120 (and accompanying flexible lumen 130) may be used as a secondary working channel and may contain the suture used in the procedure. In some embodiments, it may be large enough to accommodate secondary tools for use during the procedure for tissue acquisition or manipulation allowing secondary tool use without requiring a dedicated dual-channel delivery system such as a dual channel endoscope. If desired, a dual-channel delivery system could be used to provide even more options in a procedure. The side-saddled attachment element 120 may have an exit port in the distal assembly 14a such that secondary tools extend along an axis suitable for tissue manipulation. This axis may cross the axis of the suture carrying element, allowing a secondary tool to pull tissue into the suture carrying element's projected path. For example, this could be used to pull tissue in line with a needle to assist in driving the needle 16 through the tissue. Maintaining tension on the suture through the side-saddled attachment element 120 may keep the suture from interfering with the procedure.

Figure 10:
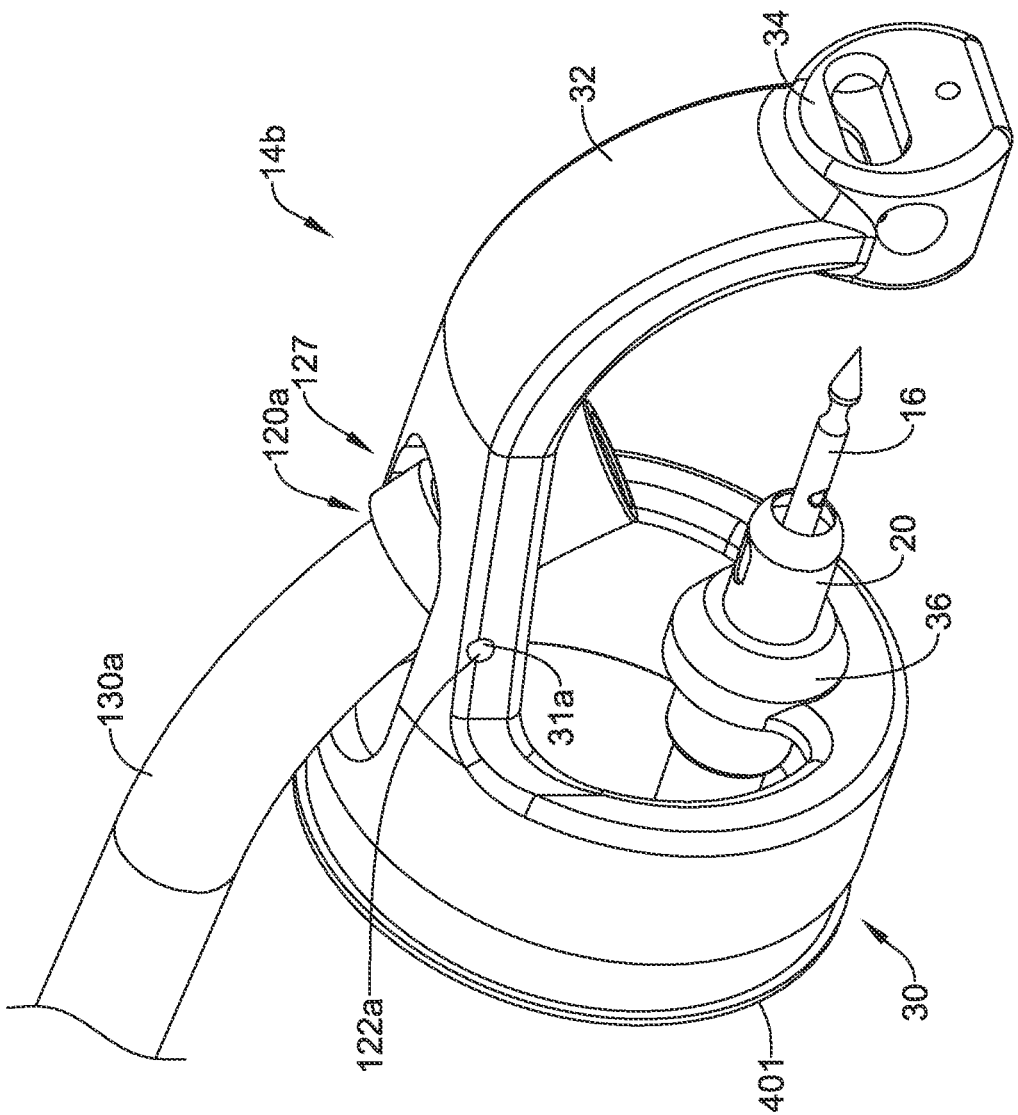
FIG. 10 is a side view of a distal assembly usable in the suture device of FIG. 1, shown with an attached lumen, in accordance with an example of the disclosure.

FIG. 10 is a perspective view of a distal assembly 14b that includes a shorter side-saddled lumen attachment element 120a that may be pivotally secured to the body 29 via one or more pegs 122a that extend into the pin apertures 31a, 31b. A lumen 130a coupled with the side-saddled lumen attachment element 120a to provide a working channel through which the suture or other tools may be extended.

Figure 12:
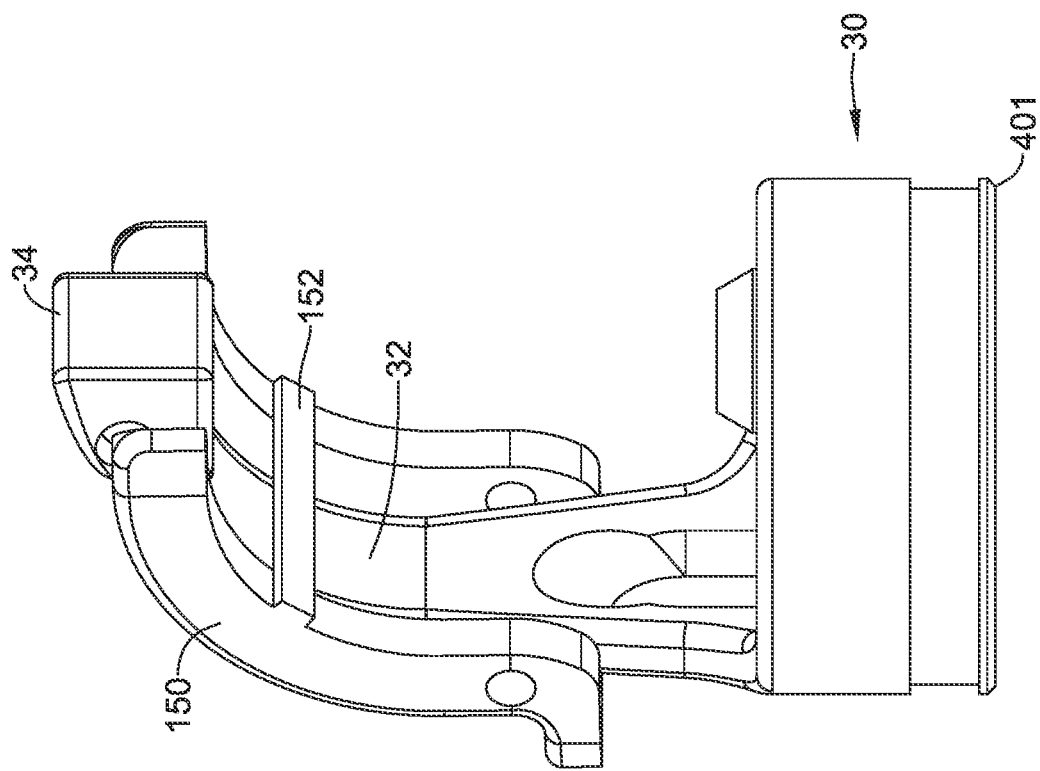
FIGS. 11 and 12 are views of a tissue release mechanism that may be used in combination with the distal assemblies of FIGS. 1 and 8 in accordance with an example of the disclosure.
Figure 11:
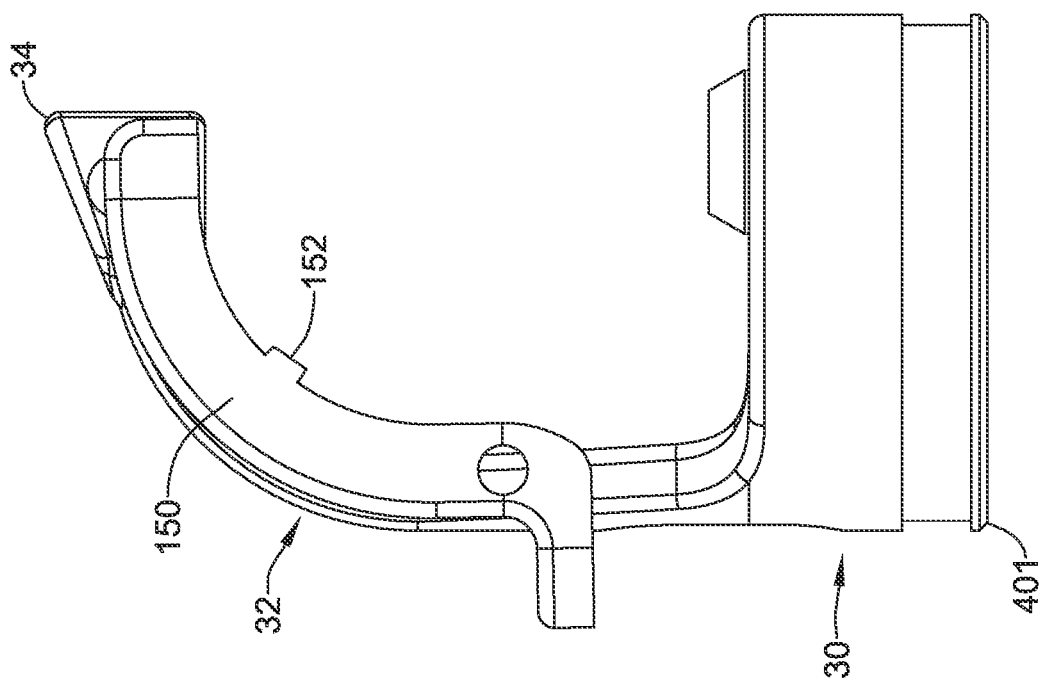

FIG. 11 and FIG. 12 are views of a tissue release mechanism 150 that may fit over the arm 32. In some embodiments, the tissue release mechanism 150 may assist in a procedure by helping to remove tissue that may otherwise become stuck on the needle 16. In some instances, the tissue release mechanism 150 may be spring-loaded to engage the needle 16, or may be separately and independently actuated. In some instances, the tissue release mechanism 150 includes a cross-bar 152 that provides an additional surface that can push tissue off of the needle 16.

In preparing the suture device 10 for use, the distal assembly 14 may be secured to a delivery device such as an endoscope. In some embodiments, an attachment enabler, such as a flexible silicone tube, may be unrolled along the delivery device in order to hold the distal assembly 14 in place and to prevent rotation of the distal assembly 14 relative to the delivery device. In some embodiments, if desired, the side-saddled lumen attachment element 120 (or 120a) may be secured to the distal assembly 14. The suture may be passed through the needle 16, and fed back towards the user interface. The device 10 may be extended through the body to the defect site.

Figure 13:
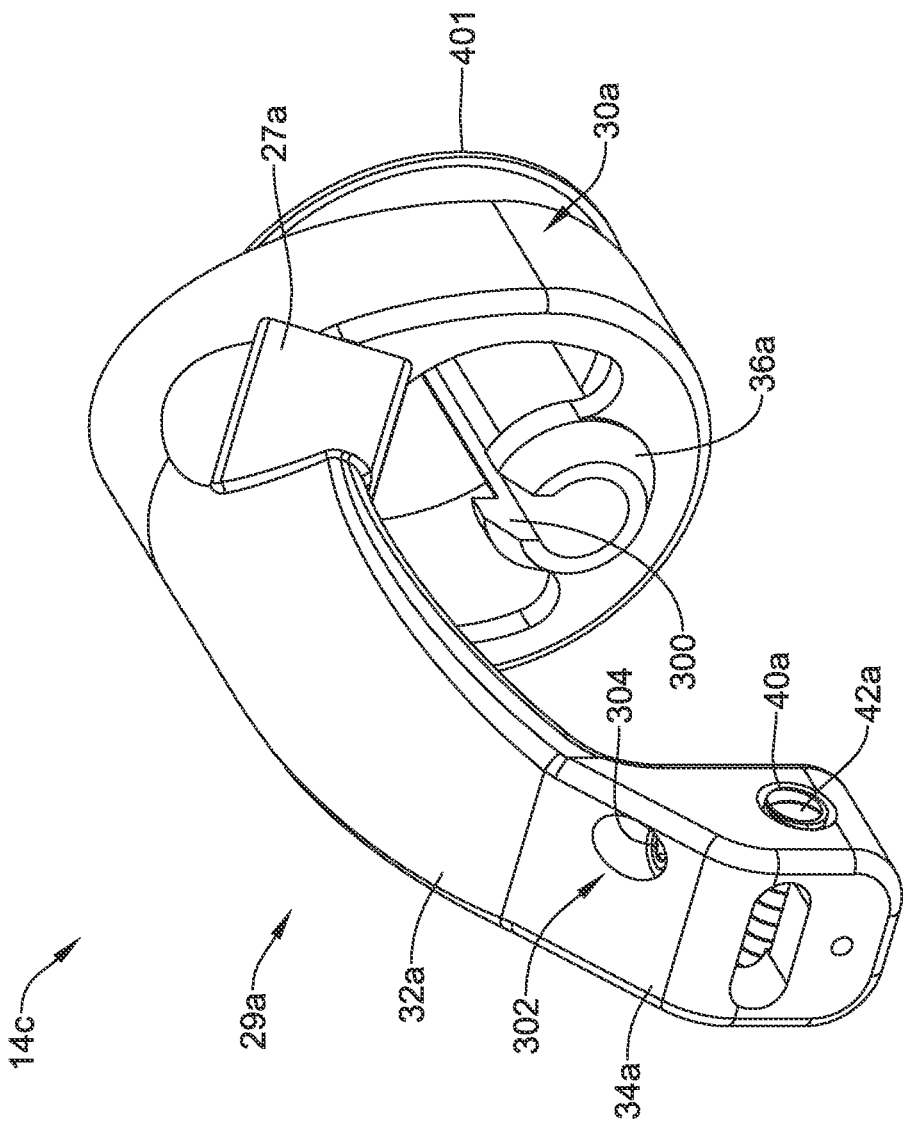
FIG. 13 is a perspective view of a distal assembly usable in the suture device of FIG. 1 in accordance with an example of the disclosure.

FIG. 13 is a perspective view of a distal assembly 14c that may, for example, be usable in the suture device 10 shown in FIG. 1. The distal assembly 14c is similar to the distal assembly 14 shown in previous Figures, but includes several modifications that may be useful, particularly in bariatric revision procedures. A bariatric procedure commonly refers to a procedure in which the effective useful volume of a patient's stomach may be surgically reduced in order to effect long-term weight loss for the patient and may be performed laparoscopically. A bariatric revision procedure is a procedure, performed endoscopically, in which changes may be made to what was originally done to the patient's stomach. In some embodiments, the distal assembly 14c may also be used in other suturing procedures, such as but not limited to full tissue thickness repairs and/or partial tissue thickness repairs.

The distal assembly 14c may include a body 29a having a proximal connector 30a that may be configured to be coupled to the distal end of an endoscope or other delivery system, for example. In some embodiments, as illustrated, the proximal connector 30a may include a fixation feature such as a fixation flange 401. The body 29a includes an arm 32a that extends to an endcap 34a. In some embodiments, the body 29a, including the arm 32a, may be similar to the body 29 and arm 32 referenced previously with respect to the distal assembly 14, the distal assembly 14a and the distal assembly 14b. In some instances, however, the body 29a and the arm 32a may be adapted to accommodate thicker tissue, which may for example mean a change in the overall shape of the body 29a and/or the arm 32a relative to the body 29 and/or the arm 32. In some embodiments, the body 29a and/or the arm 32a may simply be larger in order to accommodate thicker tissue. The distal assembly 14c may be considered as including a guide member 36a that may be secured to or integrally formed with the body 29a, and may be configured to permit a suture translation assembly (such as the suture translation assembly 12, a suture translation assembly 12a, shown in FIG. 14 through FIG. 18, or a suture translation assembly 12b, shown in FIG. 19 through FIG. 22) to extend through the guide member 36a and to translate relative to the guide member 36a.

In some embodiments, as illustrated, the guide member 36a includes a channel 300. In some embodiments, the channel 300 permits a suture to pass between the suture translation assembly 12, 12a, 12b and a working channel of the endoscope or other delivery device to which the distal assembly 14c is attached. The channel 300 may, for example, be designed to include a lead in that would help to align the suture with the channel 300 when passing the suture translation assembly 12, 12a, 12b through the working channel of the endoscope or other delivery device. In some embodiments, there may be a desire to load the suture before passing the suture translation assembly 12, 12a, 12b through the working channel of the endoscope or other delivery device.

In some instances, the distal assembly 14c includes a guide structure 27a that is attached to or integrally formed with the body 29a. In some embodiments, the guide structure 27a may instead be pivotably attached to the body 29a. The guide structure 27a may be configured to accommodate a polymeric tubular member attached thereof, in order to guide tools through the endoscope and into position relative to the working site. In some instances, the guide structure 27a may be configured to accommodate a metallic tubular member attached thereto. In some embodiments, for example, the guide structure 27a and accompanying tubular member (not illustrated) may accommodate a graspers or similar tool that allows a user to grasp tissue and pull it into position so that the needle 16 may be passed through the tissue. In some embodiments, the relative position, or offset of the guide structure 27a, relative to the relative position or offset illustrated with respect to the distal assembly 14, the distal assembly 14a or the distal assembly 14b, may be greater in order to provide more room for tools and/or to accommodate larger and/or thicker portions of tissue.

The end cap 34a includes one or more securement openings 40a that may be, as can be seen, be arranged orthogonally to a proximal needle opening (not illustrated), such as the proximal needle opening 37 illustrated for example in FIG. 3. One or more securements 42a may correspondingly be disposed within the one or more securement openings 40a. In some embodiments, the one or more securements 42a may be a coil spring that is disposed within the one or more securement openings 40a. The securement 42a may releasably engage a detent on the needle 16, as discussed with respect to the distal assembly 14.

In some embodiments, the securement opening 40a visible on one side (in the illustrated orientation) may have a diameter that is greater than an overall diameter of the securement 42a and the securement opening 40a may taper to a diameter on the opposite side (not seen) that is about the same as the diameter of the securement 42a. In some embodiments, the securement 42a may be welded, soldered, adhesively secured or otherwise attached at the left side of the securement opening 40a, and may be free to move somewhat at the right side of the securement opening 40a. In some instances, the distal assembly 14c may include an opening 302 that is orthogonal to the securement opening 40a. The opening 302 may be threaded in order to threadedly engage a set screw 304. In some embodiments, as illustrated, the opening 302 may be offset closer to the right side of the securement opening 40a, away from the secured end of the securement 42a, such that the set screw 304 may be considered as supporting the free end of the securement 42a. Rotating the set screw 304 in a first direction, such as clockwise, may cause the set screw 304 to translate towards the securement 42a, thereby increasing an interference between the securement 42a and the needle 16 and increasing a retentive force that can be applied to the needle 16. Conversely, rotating the set screw in a second direction, such as counter-clockwise, may cause the set screw 304 to translate away from the securement 42a, thereby decreasing the retentive force that can be applied to the needle 16. This may help to adjust for manufacturing tolerances, for example.

Figure 14:
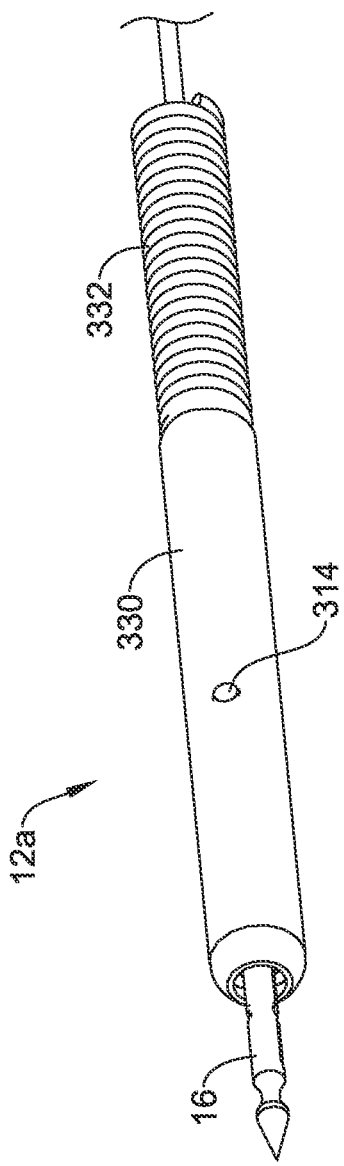
FIG. 14 is a perspective view of a suture translation assembly usable in the suture device of FIG. 1 in accordance with an example of the disclosure.
Figure 15:
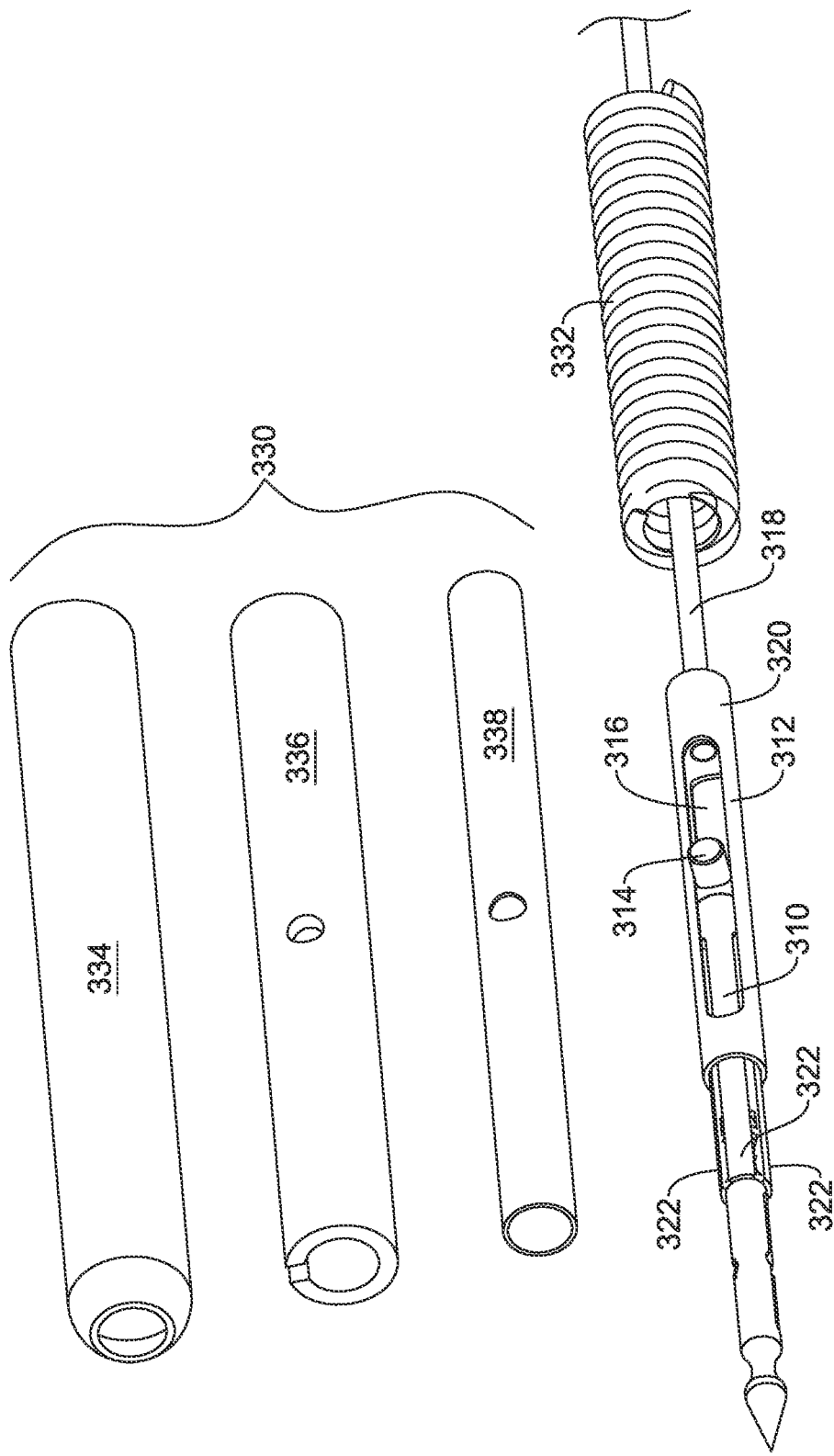
FIG. 15 is a partially exploded perspective view of the suture translation assembly of FIG. 14 in accordance with an example of the disclosure.

As noted, the distal assembly 14c may be used in combination with the suture translation assembly 12 discussed previously with respect to FIG. 5, for example. The distal assembly 14c may also be used with a suture translation assembly 12a, shown in FIG. 14 through FIG. 18, as well as with a suture translation assembly 12b, shown in FIG. 19 through FIG. 22. FIG. 14 is a perspective view of the suture translation assembly 12a, shown holding the needle 16, while FIG. 15 is a partially exploded view of the suture translation assembly 12a. As better seen in FIG. 15, the suture translation assembly 12a includes an inner member 310 that hold the needle 16. A locking member 312 is slidingly disposed over the inner member 310. As can be seen, the inner member 310 includes a pin 314 that extends radially outwardly from the inner member 310 and extends through a corresponding slot 316 that is formed in the locking member 312. The pin 314 serves to prevent relative rotation between the inner member 310 and the locking member 312. The pin 314 also serves to limit translation of the locking member 312 relative to the inner member 310.

A control member 318 is secured relative to a proximal end 320 of the locking member 312, and extends distally to a handle such as the translating handle 26 (FIG. 1). As a result, the locking member 312 may be translated distally and/or proximally relative to the inner member 310. As seen in FIG. 14, the suture translation assembly 12a includes an outer sleeve 330 that may be pinned via the pin 314 to the inner member 310. The outer sleeve 330 may be coupled with a coil 332, for example. In some embodiments, the outer sleeve 330 may be a single tubular member. In some embodiments, as shown for example in FIG. 15, the outer sleeve 330 may actually include one or more of an outer sleeve 334, a slotted sleeve 336, and an inner outer sleeve 338. The slotted sleeve 336 may be configured to permit a suture to pass therethrough. This is merely illustrative, and is not intended to be limiting in any fashion.

Figure 16:
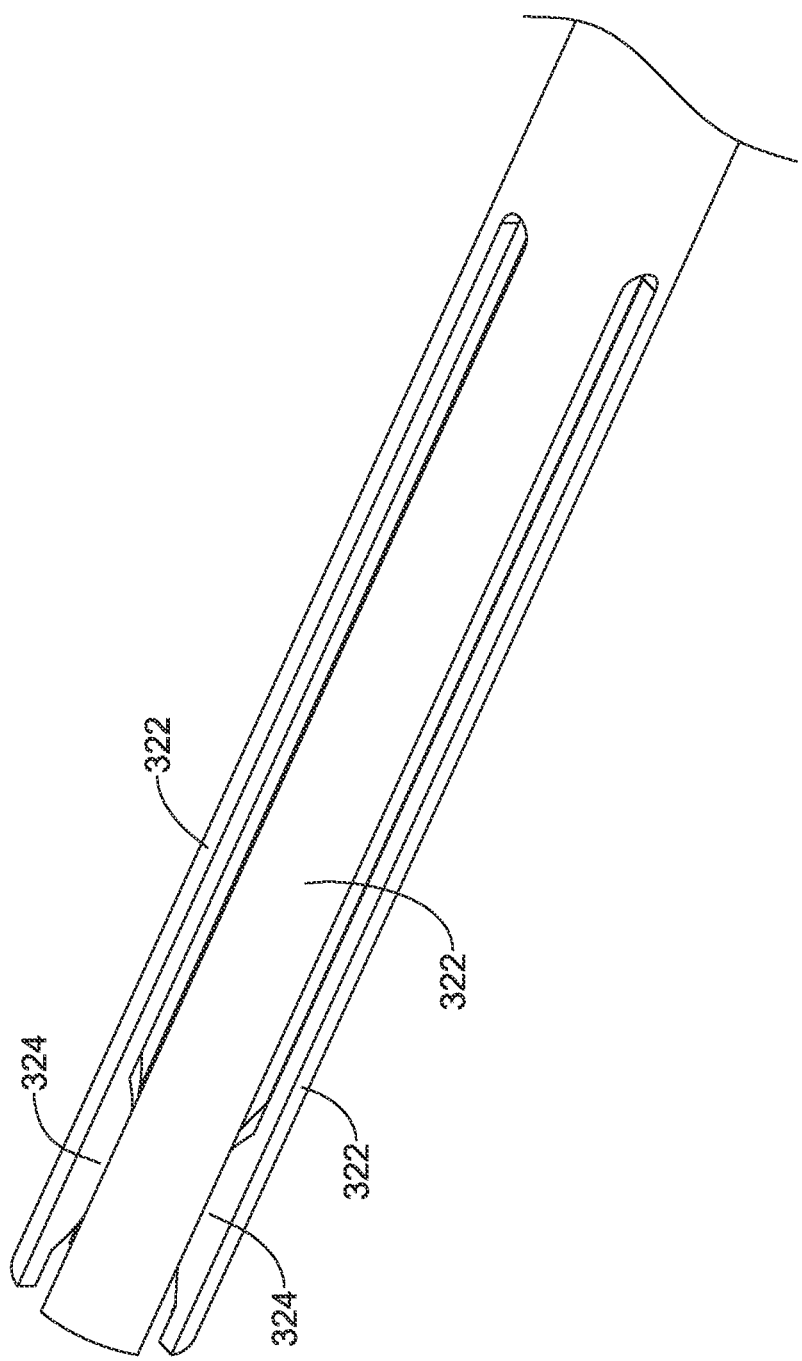
FIG. 16 is a perspective view of an inner member forming a portion of the suture translation assembly of FIG. 14 in accordance with an example of the disclosure.
Figure 17:
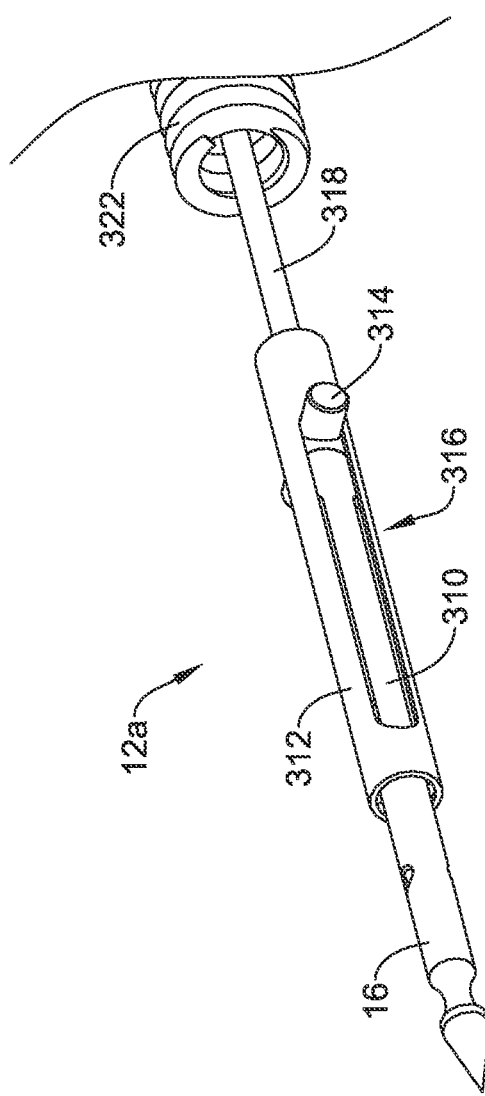
FIG. 17 is a perspective view of a portion of the suture translation assembly of FIG. 14, shown in a locked configuration in accordance with an example of the disclosure.
Figure 18:
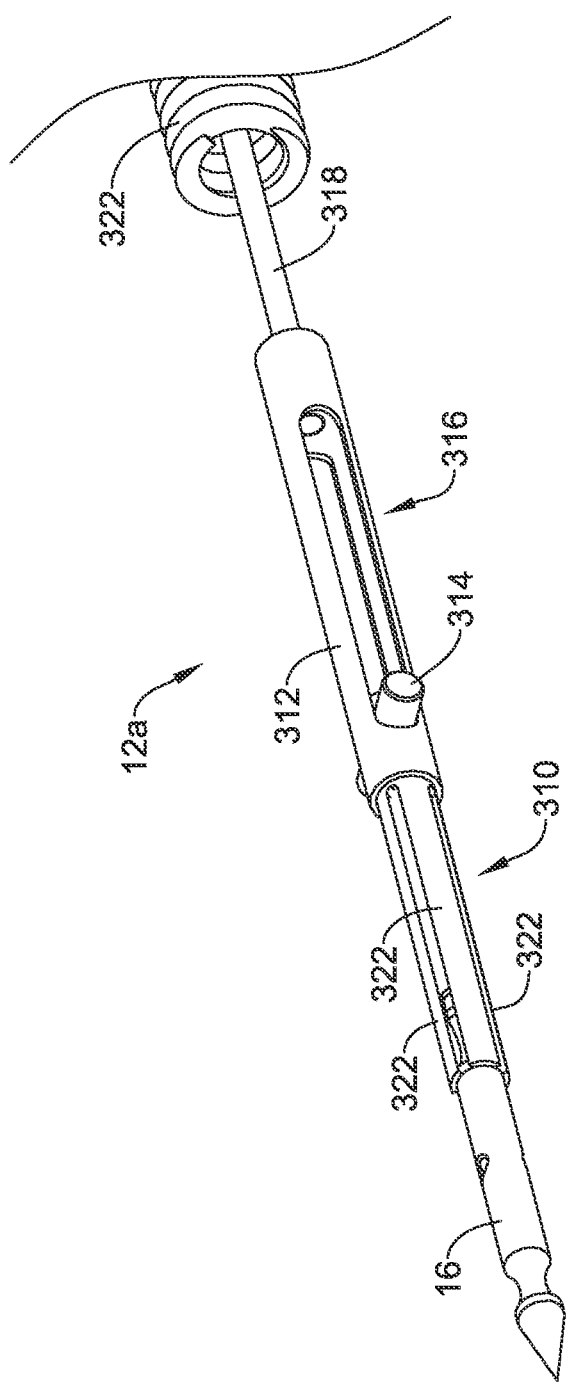
FIG. 18 is a perspective view of a portion of the suture translation assembly of FIG. 14, shown in an unlocked configuration in accordance with an example of the disclosure.

The inner member 310 includes several arms 322 that, as seen in FIG. 16, which shows the distal portion of the inner member 310, include curved tabs 324 that are configured to engage corresponding detents within the needle 16. While a total of four arms 322 are shown, it will be appreciated that the inner member 310 may include any number of arms 322. It will be appreciated that the arms 322 are relatively long in length, and as a result may be considered as being relatively flexible. With the locking member 312 extended distally into a locking configuration, as shown for example in FIG. 17, the locking member 312 prevents outward movement of the arms 322. As a result, the curved tabs 324 remain in engagement with the corresponding detents of the needle 16, and the needle 16 remains locked to the suture translation assembly 12a. With the locking member 312 retracted proximally into an unlocked configuration, as shown for example in FIG. 18, the arms 322 are free to move radially outwardly, thereby releasing the curved tabs 324 from the detents in the needle 16, and allowing the needle 16 to move distally relative to the inner member 310.

Figure 19:
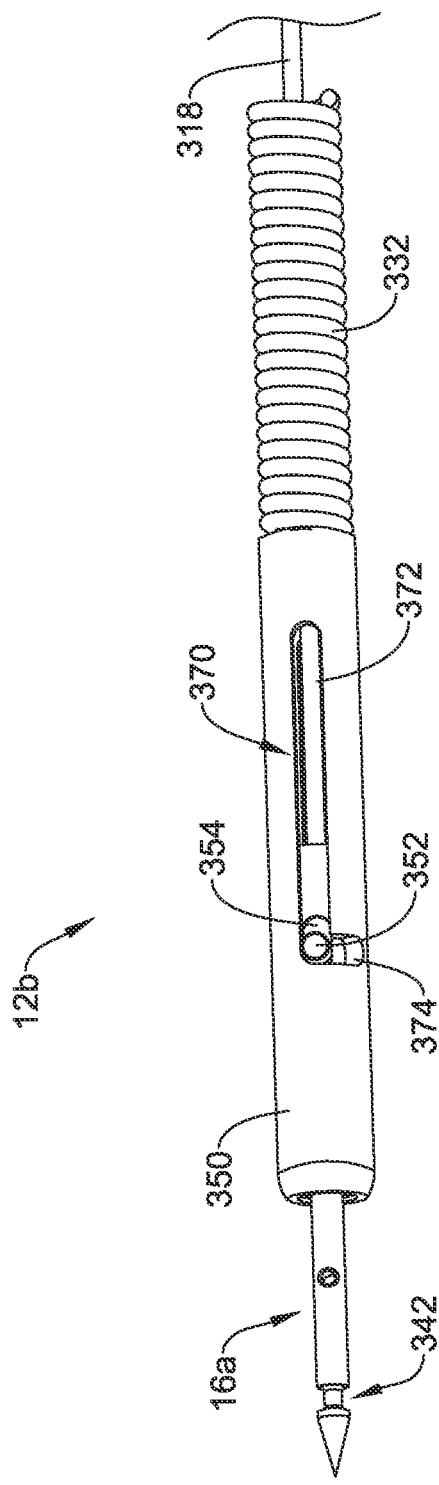
FIG. 19 is a perspective view of a suture translation assembly usable in the suture device of FIG. 1 in accordance with an example of the disclosure.
Figure 20:
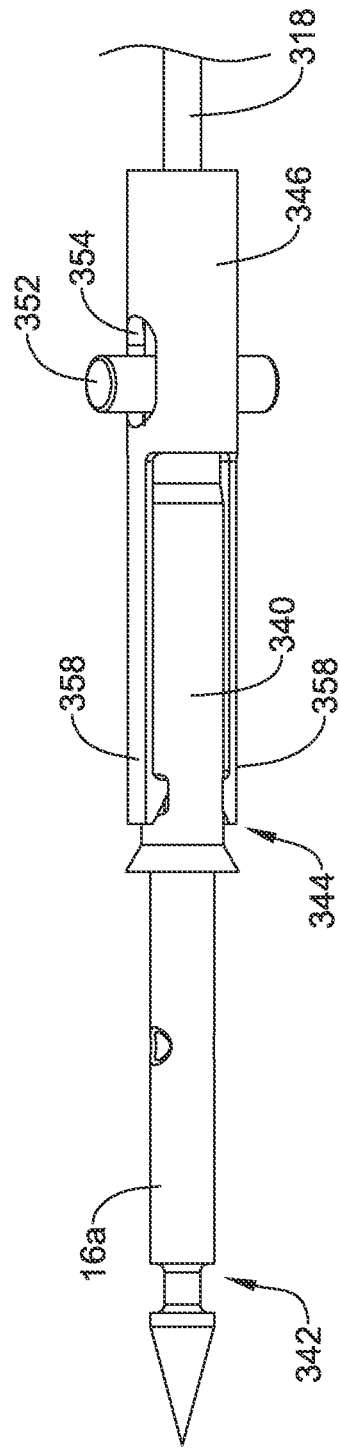
FIG. 20 is a perspective view of the suture translation assembly of FIG. 19, shown with some elements removed to show internal structure, with the suture translation assembly shown in a locked configuration in accordance with an example of the disclosure.

FIG. 19 is a perspective view of a suture translation assembly 12b that may be used in combination with any of the distal assembly 14, the distal assembly 14a, the distal assembly 14b and/or the distal assembly 14c. FIG. 20 is a perspective view of the suture translation assembly 12b with outer portions such as an outer sleeve 350 (FIG. 19) removed to reveal an inner member 340 that holds a needle 16a. In some embodiments, the outer sleeve 350 may be a single tubular member. In some instances, the outer sleeve 350 may include several elements, such as described with respect to the outer sleeve 330 (FIG. 15).

In some embodiments, as illustrated, the needle 16a has a distal detent 342 and a proximal detent 344 (visible in FIG. 21) that are shaped differently than the corresponding detents in the needle 16. The suture translation assembly 12b includes a locking member 346 that is slidingly disposable relative to the inner member 340. The pin 352 is attached to the inner member 340 and extends through a corresponding slot 354 formed in the locking member 342. The pin 352 limits translation of the locking member 342 relative to the inner member 340, and also prevents relative rotational movement of the locking member 342. The locking member 342 is secured to the control member 318, which extends distally to a handle such as the translating handle 26 (FIG. 1). As a result, the locking member 342 may be translated distally and/or proximally relative to the inner member 340.

In some embodiments, the outer sleeve 350 may define a slot 370 including an axially extending slot portion 372 and a shorter radially extending slot portion 374. In some embodiments, the axially extending slot portion 372 permits the pin 352 to move within the axially extending slot portion 372 in order to permit the needle 16a to be fully withdrawn into the suture translation assembly 12b for advancement through an endoscope or other delivery device. Once the suture translation assembly 12b has been advanced through the endoscope or other delivery device, the inner member 340 and the locking member 342 may be advanced distally through the outer sleeve 350 until the pin 352 aligns with the radially extending slot portion 374. By rotating the translating handle 26, the pin 352 may be rotated into position within the radially extending slot portion 374 so that the locking member 342 may be translated relative to the inner member 340.

Figure 21:
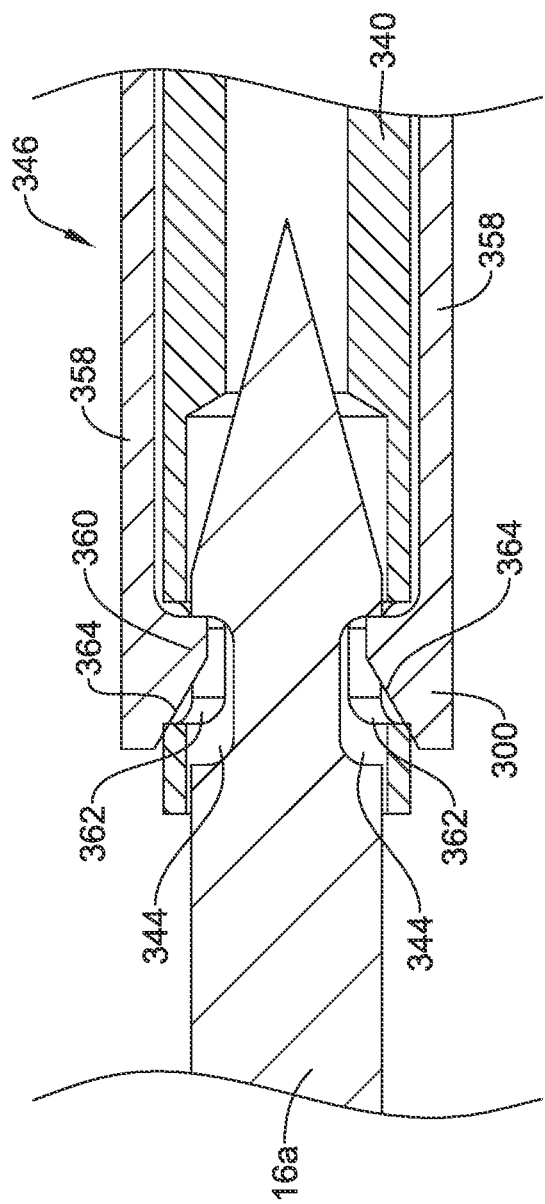
FIG. 21 is a side view of a portion of the suture translation assembly of FIG. 19, showing how a locking member engages an inner member of the suture translation assembly and a needle in the locked configuration as shown in FIG. 20 and in accordance with an example of the disclosure.

In some embodiments, as illustrated, the locking member 342 includes a pair of arms 358 that extend distally from the locking member 342. As seen for example in FIG. 21, the arms 358 include tabs 360 that, when the suture translation assembly 12b is in a locked configuration as shown in FIGS. 20 and 21, the tabs 360 extend through slots 362 formed within the inner member 340. As a result, the tabs 360 are able to extend through the slots 362 and engage the proximal detent 344 of the needle 16a. While a pair of arms 358 are illustrated, it will be appreciated that the locking member 342 may include any number of arms 358, and of course a corresponding number of slots 362.

Figure 22:
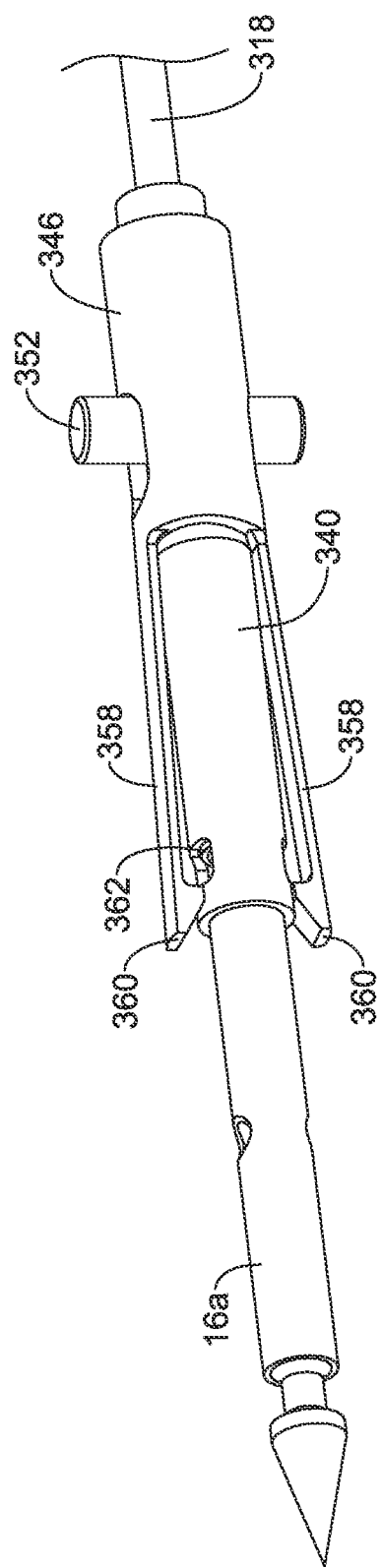
FIG. 22 is a perspective view of the suture translation assembly of FIG. 19, shown in an unlocked configuration in accordance with an example of the disclosure.

In order to move the suture translation assembly 12b into an unlocked configuration, as shown for example in FIG. 22, the locking member 342 may be moved distally relative to the inner member 340. As can be seen in FIG. 22, the tabs 360 have moved out of the slots 362 (only one slot 362 is seen), and the needle 16a is free to move relative to the suture translation assembly 12b. As the locking member 342 moves distally, angled surfaces 364 push against the slots 362 and are moved outwardly.

In some embodiments, and with respect to FIG. 13, the guide member 36a includes a channel 300 that is configured to permit a suture to pass between the suture translation assembly 12, 12a, 12b and a working channel of the endoscope or other delivery device to which the distal assembly 14c is attached. The channel 300 may, for example, be designed to include a lead in that would help to align the suture with the channel 300 when passing the suture translation assembly 12, 12a, 12b through the working channel of the endoscope or other delivery device. In some embodiments, there may be a desire to load the suture before passing the suture translation assembly 12, 12a, 12b through the working channel of the endoscope or other delivery device.

Figure 23:
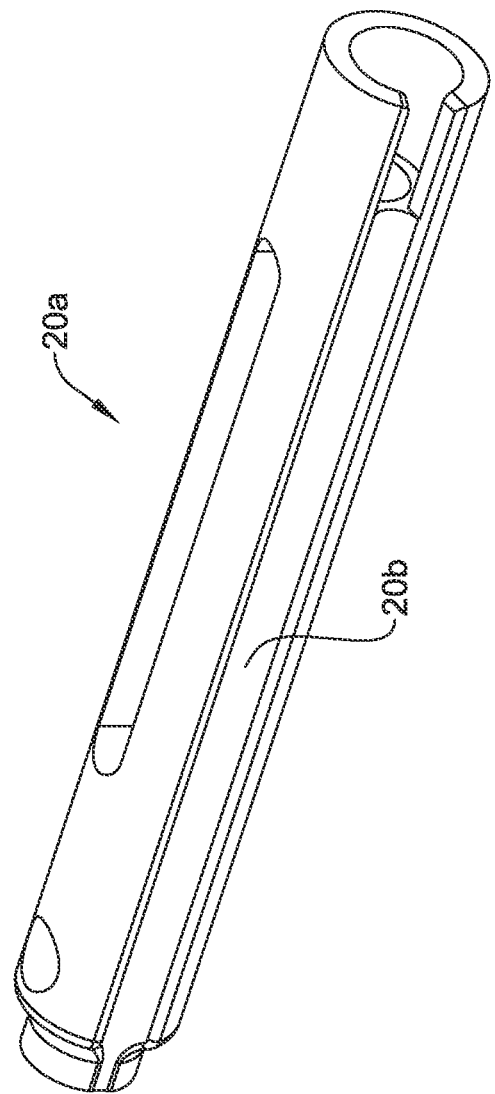
FIG. 23 is a perspective view of a sleeve usable as part of a suture translation assembly.
Figure 24:
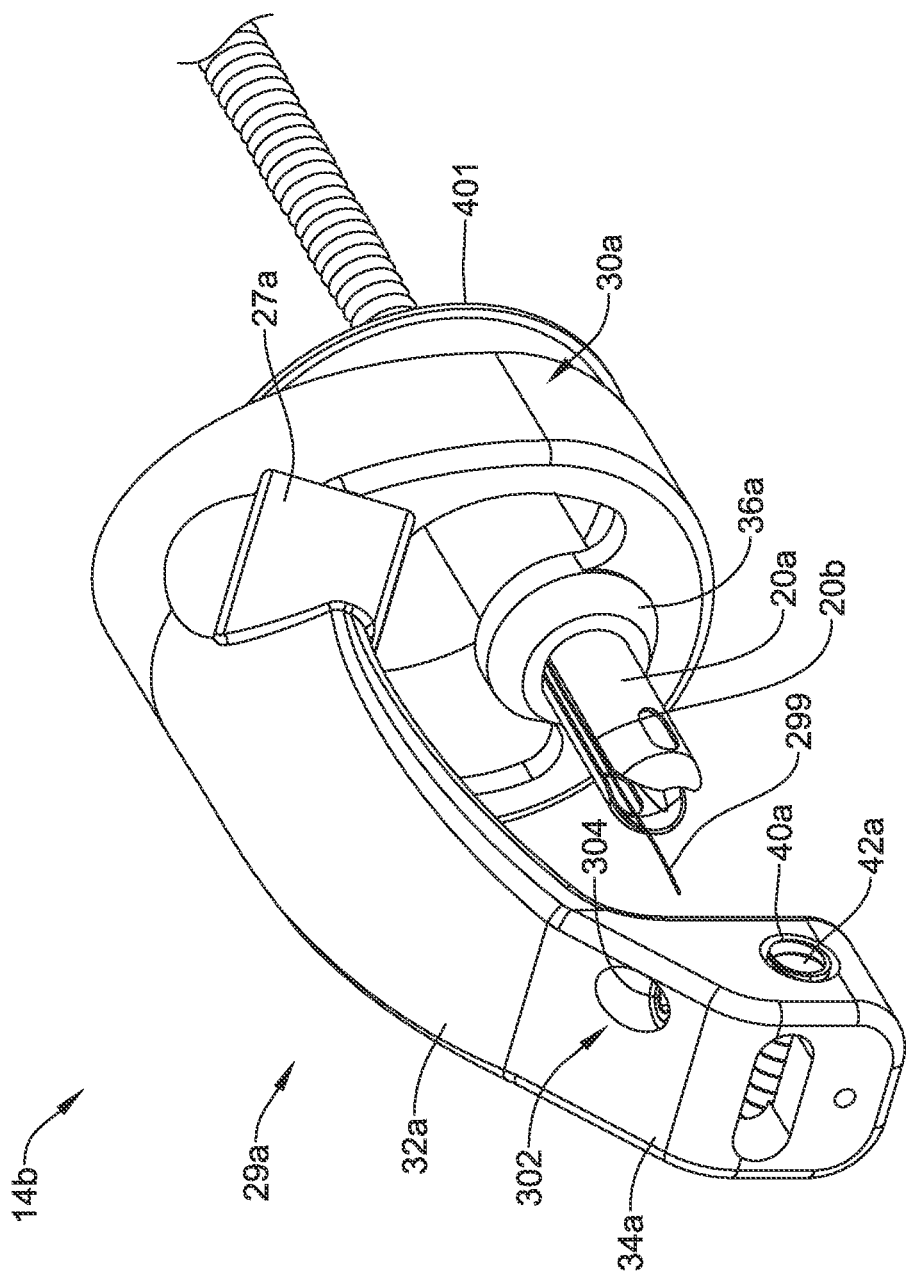
FIG. 24 is a perspective view of a distal assembly utilizing the sleeve of FIG. 23 and usable in the suture device of FIG. 1 in accordance with an example of the disclosure.

In some instances, as shown for example in FIG. 23, instead of putting a channel 300 in the guide member 36a, the suture translation assembly 12, 12a, 12b may be modified to accommodate a suture passing along the suture translation assembly 12, 12a, 12b. FIG. 24 is a perspective view of a sleeve 20a that may be used in forming a part of the suture translation assembly 12, 12a, 12b. It can be seen that the sleeve 20a includes a groove 20b that extends a length of the sleeve 20a. FIG. 24 shows the sleeve 20a extending through the guide member 36a, with a suture 299 extending through the groove 20b.

Figure 25:
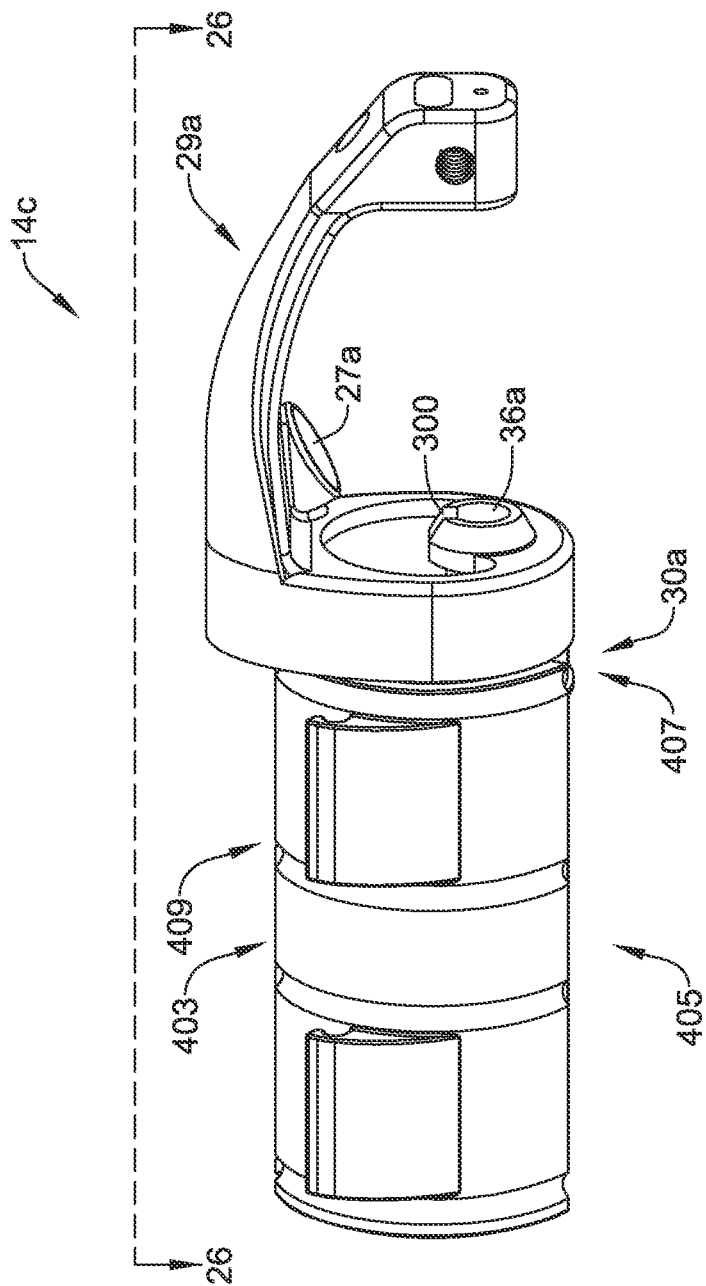
FIG. 25 is a perspective view of a distal assembly in combination with a split ring attachment mechanism in accordance with an example of the disclosure.
Figure 26:
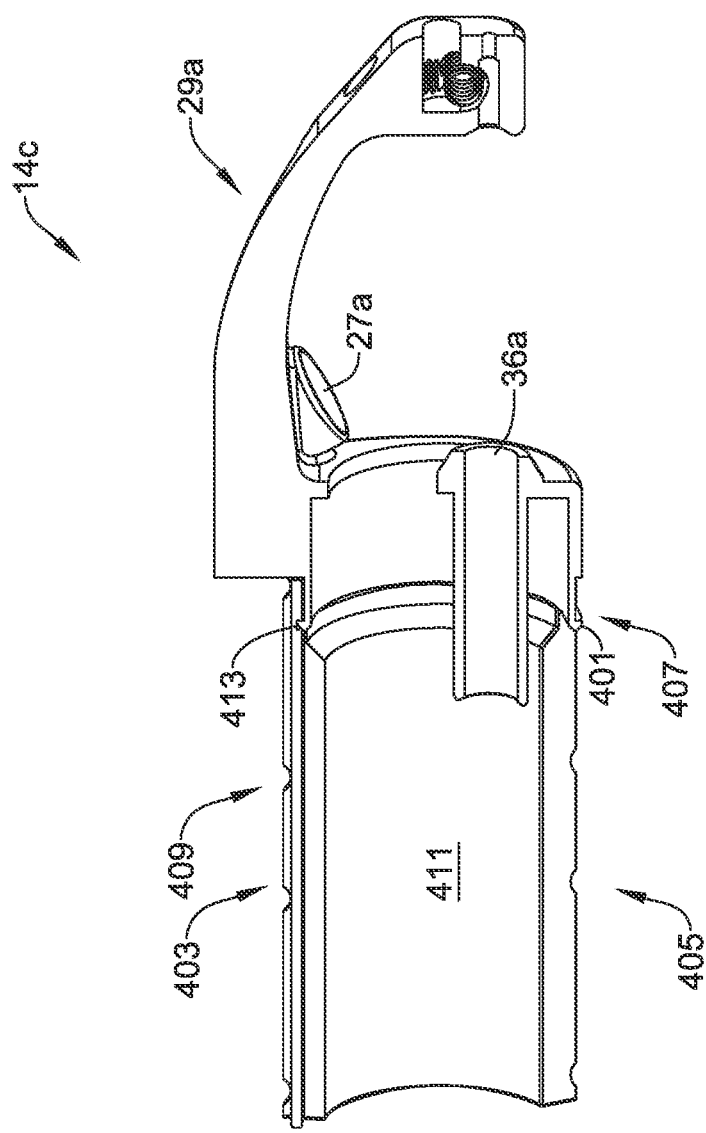
FIG. 26 is a cross-sectional view of the distal assembly in combination with the split ring attachment mechanism of FIG. 25, taken along line 26-26.
Figure 27:
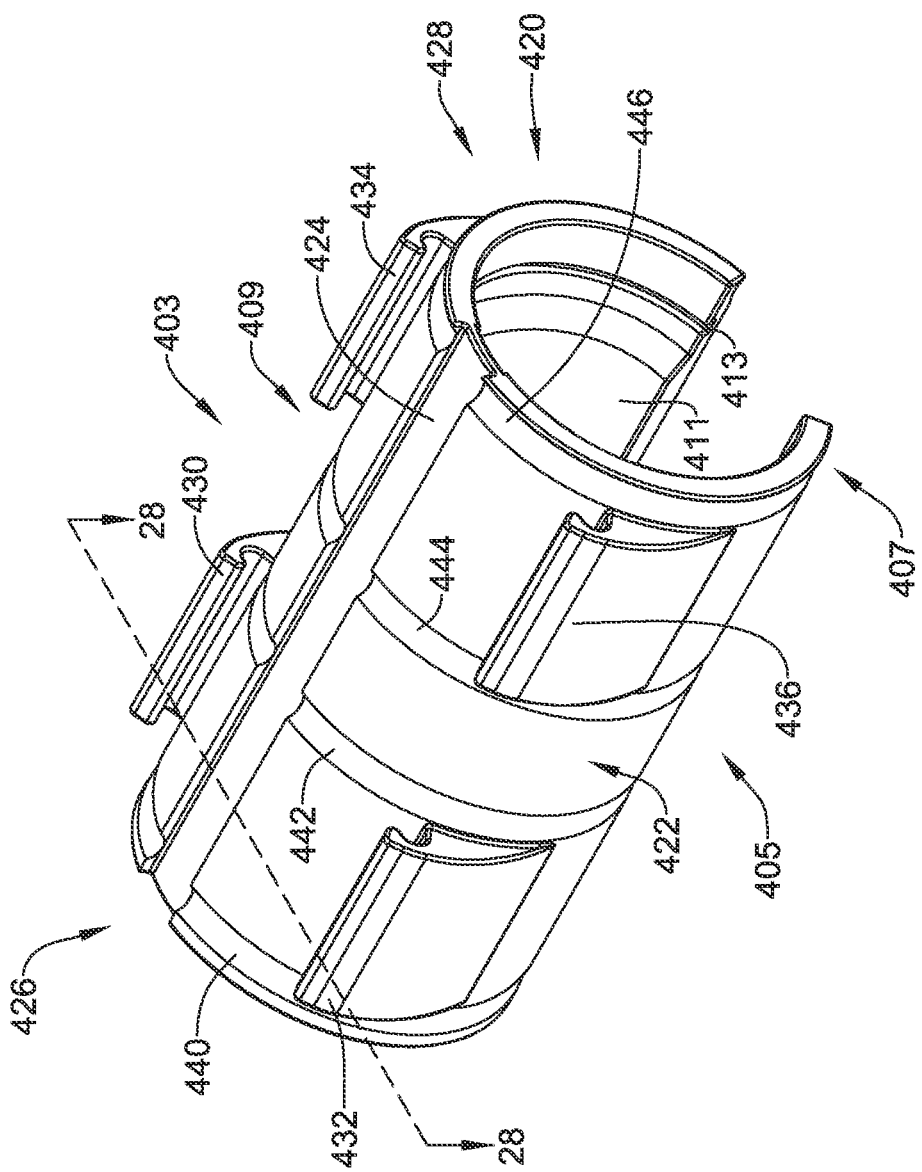
FIG. 27 is a perspective view of the split ring attachment mechanism of FIG. 25.

In some embodiments, movement of the suture translation assembly 12, 12a, 12b relative to the distal assembly 14, 14a, 14b, 14c, particularly as the needle 16, 16a is passed back and forth between the suture translation assembly 12, 12a, 12b and the distal assembly 14, 14a, 14b, 14c, may potentially interfere with securement of the distal assembly 14, 14a, 14b, 14c relative to the endoscope or other delivery system. FIG. 25 is a perspective view of the distal assembly 14c coupled to a split ring attachment mechanism 403 and FIG. 26 is a cross-sectional view thereof, taken along line 26-26 of FIG. 25. FIG. 27 is a perspective view of the split ring attachment mechanism 403. In some embodiments, and as will be discussed in greater detail, the split ring attachment mechanism 403 may be considered as including an endoscope engaging portion 405 that is adapted to engage an endoscope in a compressive fit and a distal endcap engaging portion 407 that is adapted to engage the distal endcap, or distal assembly 14c, in an interference fit. It will be appreciated that the split ring attachment mechanism 403 may be used in combination with any of the distal assemblies 14, 14a, 14b, 14c. While discussed and illustrated with respect to use with the suture device 10, it will be appreciated that the split ring attachment mechanism 403 may be used in combination with other devices that one may wish to releasably secure to an endoscope or other delivery system.

In some embodiments, the split ring attachment mechanism 403 may be considered as including an elongate body 409 that largely defines the endoscope engaging portion 405. In some embodiments, as seen for example in FIGS. 26 and 27, the elongate body 409 includes an inner surface 411 that may be considered as being adapted to frictionally engage an outer surface of an endoscope to which the split ring attachment mechanism 403 is being secured. In some embodiments, the elongate body 409 may have a length that is selected to provide a maximum amount of surface area for the inner surface 411 while not interfering with the flexibility of the endoscope or other delivery system. The overall dimensions of the elongate body 409 may vary, depending on particulars of the endoscope to which it will be attached, but in some embodiments the elongate body 409 may have an overall length that is in a range of about 0.4 inches to about 1.2 inches and a diameter that is in a range of about 0.3 inches to about 0.6 inches. These are just examples.

While the inner surface 411 is shown as having a largely cylindrical profile, for being secured to an endoscope having a largely cylindrical outer surface, it will be appreciated that in some embodiments the elongate body 409 and/or the inner surface 411 thereof may have a different profile that is complementary to an endoscope having a non-cylindrical outer surface, for example.

In some embodiments, the split ring attachment mechanism 403 may include an annular slot 413 that is complementary in position and dimension in order to accommodate the fixation feature or flange 401 that forms part of the proximal connector 30. As can be seen in FIG. 26, when the split ring attachment mechanism 403 is in its locked configuration (as illustrated), the fixation feature or flange 401 fits into the annular slot 413 and limits relative axial movement of the distal assembly 14c relative to the split ring attachment mechanism 403 and thus limits relative axial movement of the distal assembly 14c relative to the endoscope or other delivery system to which the split ring attachment mechanism 403 and the distal assembly 14c are secured. As alluded to, the split ring attachment mechanism 403 may be considered as being movable between a locked configuration in which the split ring attachment mechanism 403 is locked to the distal assembly 14c and an engagement configuration that enables the split ring attachment mechanism 403 to be advanced radially over an endoscope and a distal assembly such as the distal assembly 14c already attached to the endoscope. In some embodiments, the split ring attachment mechanism 403 may be separately secured to the distal assembly 14c, and the combination may be axially advanced over a distal end of the endoscope or other delivery system.

Figure 28:
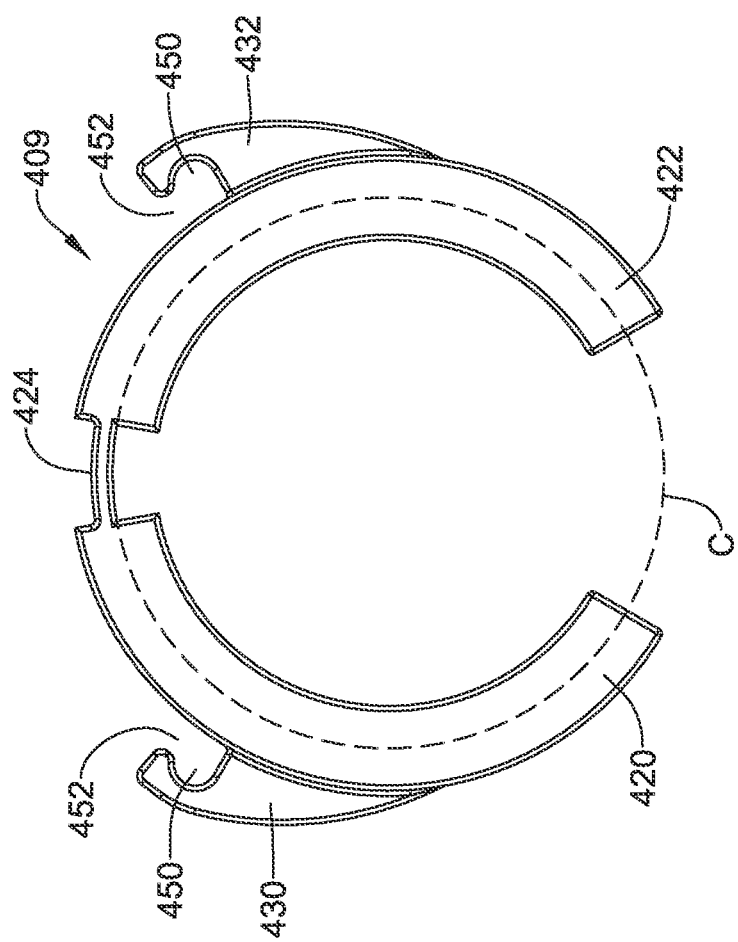
FIG. 28 is a cross-sectional view of the split ring attachment mechanism of FIG. 27, taken along line 28-28 and showing the split ring attachment mechanism in a locking configuration.
Figure 29:
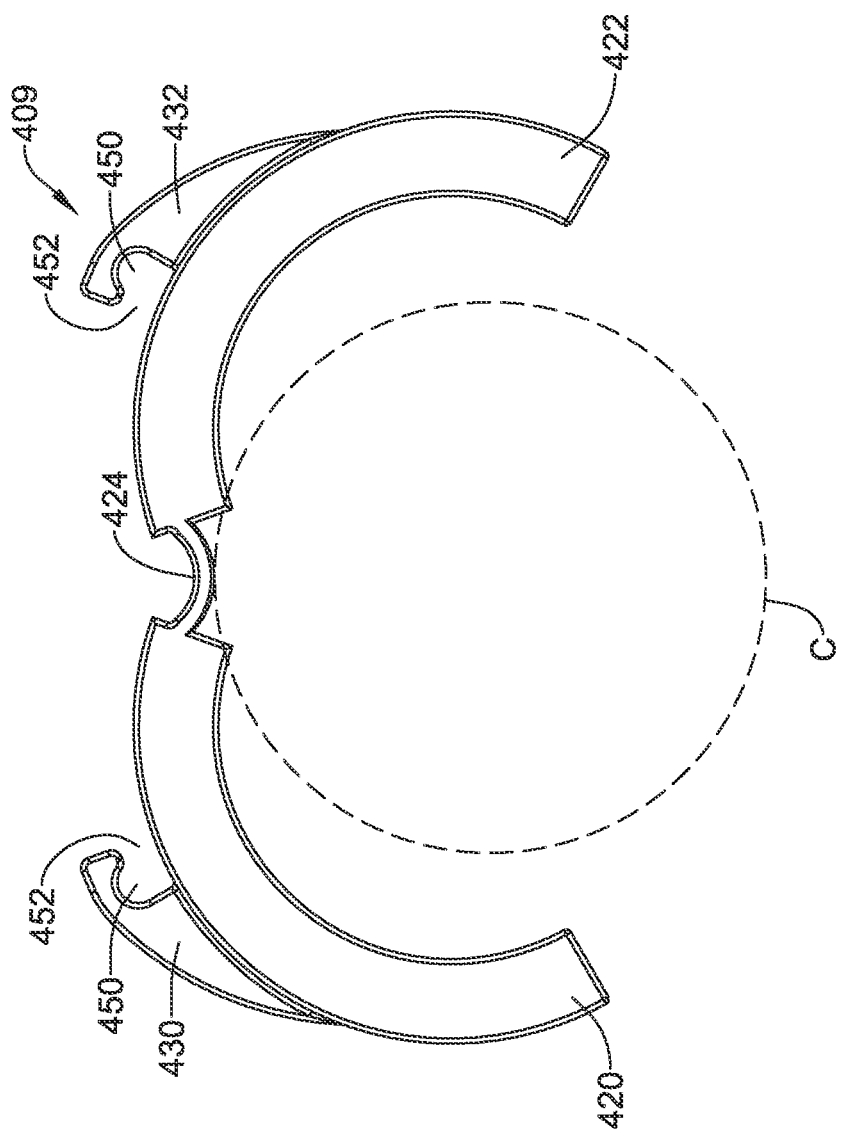
FIG. 29 is a cross-sectional view of the split ring attachment mechanism of FIG. 27, showing the split ring attachment mechanism in an engagement configuration.

FIG. 28 is a cross-sectional view of a proximal portion of the split ring attachment mechanism 403 illustrating the locked configuration while FIG. 29 is a similar view illustrating the engagement configuration. In FIG. 28, the elongate body 409 may be seen as having a first body portion or clamping portion 420 and a second body portion or clamping portion 422. A living hinge 424 enables the first clamping portion 420 and the second clamping portion 422 to move from the locked configuration shown in FIG. 28 to the engagement configuration shown in FIG. 29. It will be appreciated that in the engagement configuration, the split ring attachment mechanism 403 may be radially advanced over an endoscope and a distal assembly secured to the endoscope. In some embodiments, as shown for example in FIG. 28, that the first clamping portion 420 and the second clamping portion 422 extend along a circle C when in the locking configuration as shown. In FIG. 29, it can be seen that the first clamping portion 420 and the second clamping portion 422 are deflected away from the locking configuration, and are deflected outwardly away from the circle C.

In some embodiments, as shown, the living hinge 424 may simply be a thinner portion of the elongate body 409 that provides additional flexibility relative to the rest of the elongate body 409. In some embodiments, the living hinge 424 may be considered as extending longitudinally along the elongate body 409, as shown in FIG. 27, where the living hinge 424 may be seen as extending from a proximal end 426 of the split ring attachment mechanism 403 to a distal end 428 of the split ring attachment mechanism 403. In some instances, a mechanical hinge in which the first clamping portion 420 and the second clamping portion 422 come together in a pivoting fashion may be used in place of the living hinge 424.

As will be appreciated, once the split ring attachment mechanism 403 has been opened up, as shown in FIG. 29, and advanced radially over the endoscope and the distal assembly 14c disposed thereon, the split ring attachment mechanism 403 may be moved back into the locking configuration shown in FIG. 28. In some instances, while not illustrated, any variety of fastening mechanisms may be used to hold the split ring attachment mechanism 403 into the locking configuration. For example, a ratcheting mechanism may be used. In some embodiments, as shown, the split ring attachment mechanism 403 may be configured to accommodate one or more elastic members, such as but not limited to O-rings or rubber bands, to hold the split ring attachment mechanism 403 in the locking configuration but also to provide a compressive force such that the inner surface 411 frictionally engages the outer surface of the endoscope or other delivery system. In order to accommodate one or more elastic members, the split ring attachment mechanism 403 may include hooks.

As illustrated in FIG. 27, the split ring attachment mechanism 403 includes a first pair of opposing hooks 430 and 432 as well as a second pair of opposing hooks 434 and 436. In other cases, the split ring attachment mechanism 403 may only have a single pair of hooks, or may have two, three or more pairs of hooks. The hook 430 extends from the first clamping portion 420 while the hook 432 extends from the second clamping portion 422. It will be appreciated that an elastic member (not shown in FIG. 27) may engage the hook 430, extend radially around the split ring attachment mechanism 403 opposite the living hinge 424, and engage the hook 432. Similarly, another elastic member may engage the hook 434, which also extends from the first clamping portion 420, extend radially around the split ring attachment mechanism 403 opposite the living hinge 424.

In some embodiments, as shown in FIG. 27, the split ring attachment mechanism 403 may be configured to accommodate the elastic members. For example, the split ring attachment mechanism 403 may include annular grooves 440 and 442 in order to accommodate an elastic member extending between the hook 430 and the hook 432. Similarly, the split ring attachment mechanism 403 may include annular grooves 444 and 446 in order to accommodate an elastic member extending between the hook 434 and the hook 436. It will be appreciated that in some embodiments, the annular grooves 440, 442 and 444, 446 may help keep the elastic members from migrating axially relative to the split ring attachment mechanism 403. In some embodiments, the annular grooves 440, 442 and 444, 446 also help to minimize a diameter increase otherwise caused by the elastic members extending around the split ring attachment mechanism 403.

In some embodiments, as seen for example in FIGS. 28 and 29, the hooks 430, 432, 434, 436 may be configured to provide a frictional engagement with the elastic members. As can be seen, for example, each of the hooks 430, 432 and 434, 436 include a recess 450 configured to accommodate a diameter of an elastic member and an opening 452 to the recess 450 that is smaller than a diameter of the recess 450. This helps to hold the elastic members in place relative to the hooks 430, 432 and 434, 436. The recess 450 and the opening 452 are not labeled on FIG. 27 due to the orientation of the drawing, but are clearly visible.

Figure 30:
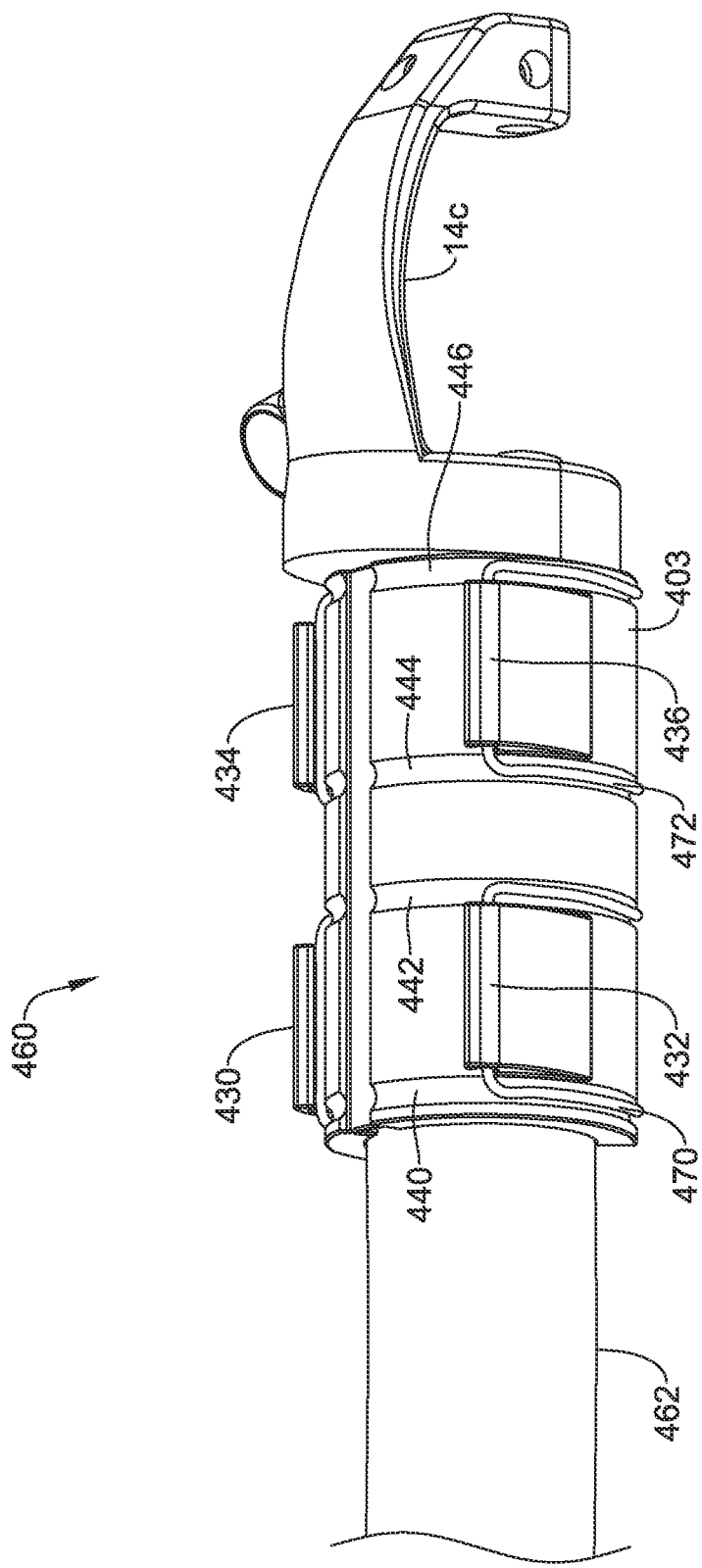
FIG. 30 is a perspective view of the distal assembly and split ring attachment mechanism of FIG. 25 shown secured on an endoscope in accordance with an example of the disclosure.

FIG. 30 is a perspective view of an assembly 460 that includes the distal assembly 14c secured to the end of an endoscope 462 via the split ring attachment mechanism 403. The assembly 460 includes a first elastic member 470 that extends from the hook 430 to the hook 432 and a second elastic member 472 that extends from the hook 434 to the hook 436. As a result of the first elastic member 470 and the second elastic member 472, the split ring attachment mechanism 403 is able to provide a compressive force against the outer surface of the endoscope 462, and thus the inner surface 411 of the split ring attachment mechanism 403 is able to provide a frictional force against the outer surface of the endoscope 462 that helps to anchor the split ring attachment mechanism 403 in place.

Figure 31:
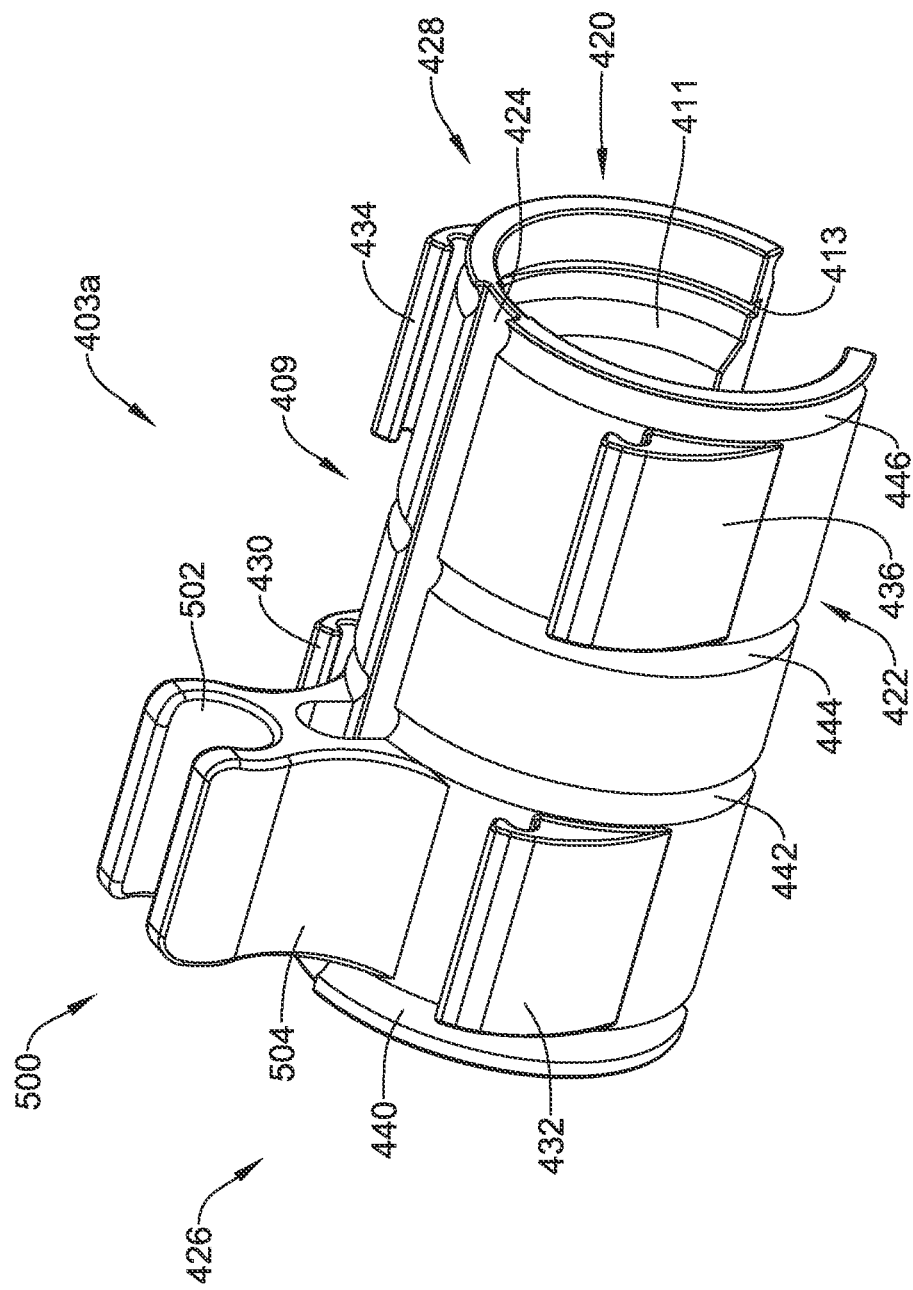
FIG. 31 is a perspective view of a split ring attachment mechanism in accordance with an example of the disclosure.

FIG. 31 is a perspective view of a split ring attachment mechanism 403a that is similar to the split ring attachment mechanism 403, but includes a clip 500 that may help to hold and/or secure an external lumen or working channel. In some embodiments, the clip 500 includes an engagement feature 502 that is configured to releasably secure an external lumen or working channel (not illustrated) in a snap fit. In some instances, as shown, the clip 500 also includes a body portion 504 that spaces the engagement feature 502 away from the split ring attachment mechanism 403a. While the clip 500 is illustrated as spanning the living hinge 423, in some embodiments the clip 500 may be radially offset from the illustrated position.

Figure 32:
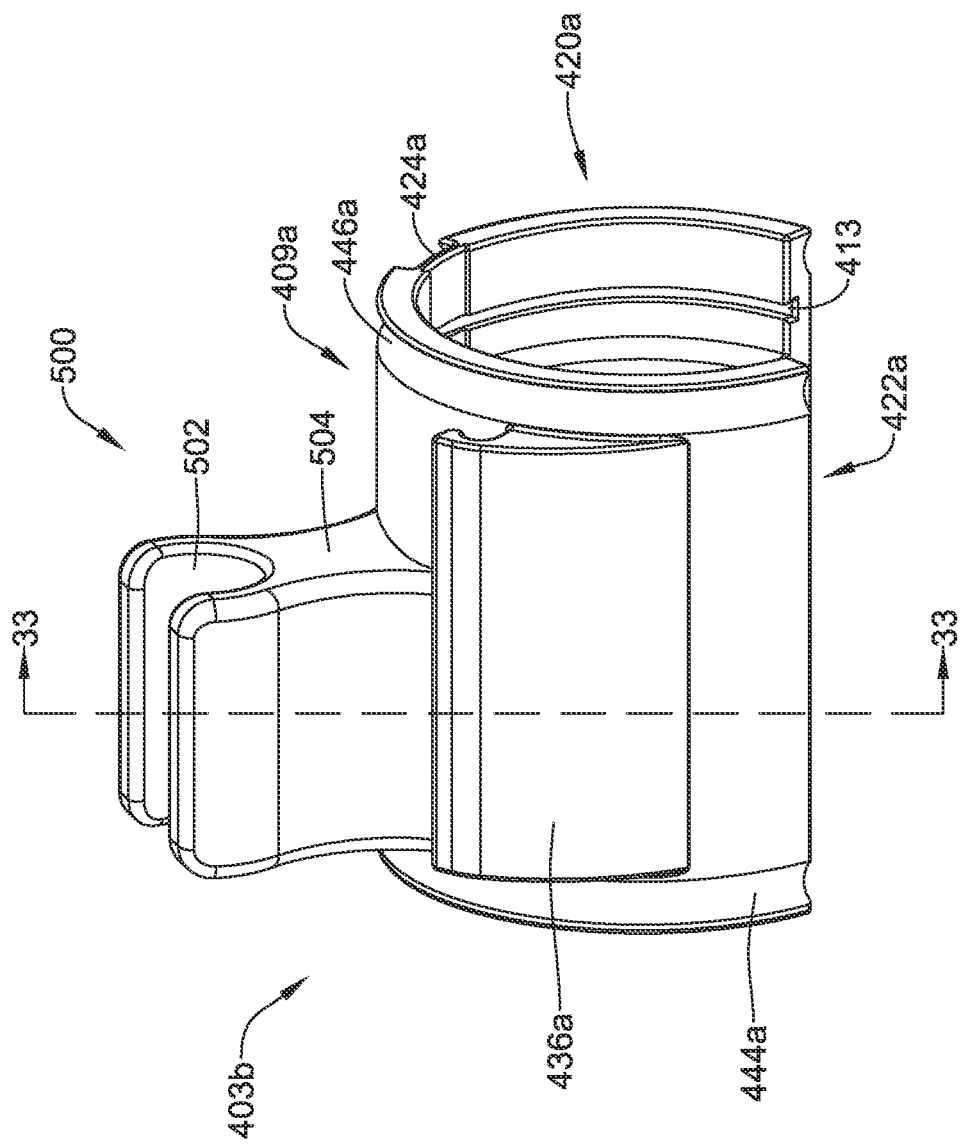
FIG. 32 is a perspective view of a split ring attachment mechanism in accordance with an example of the disclosure.
Figure 33:
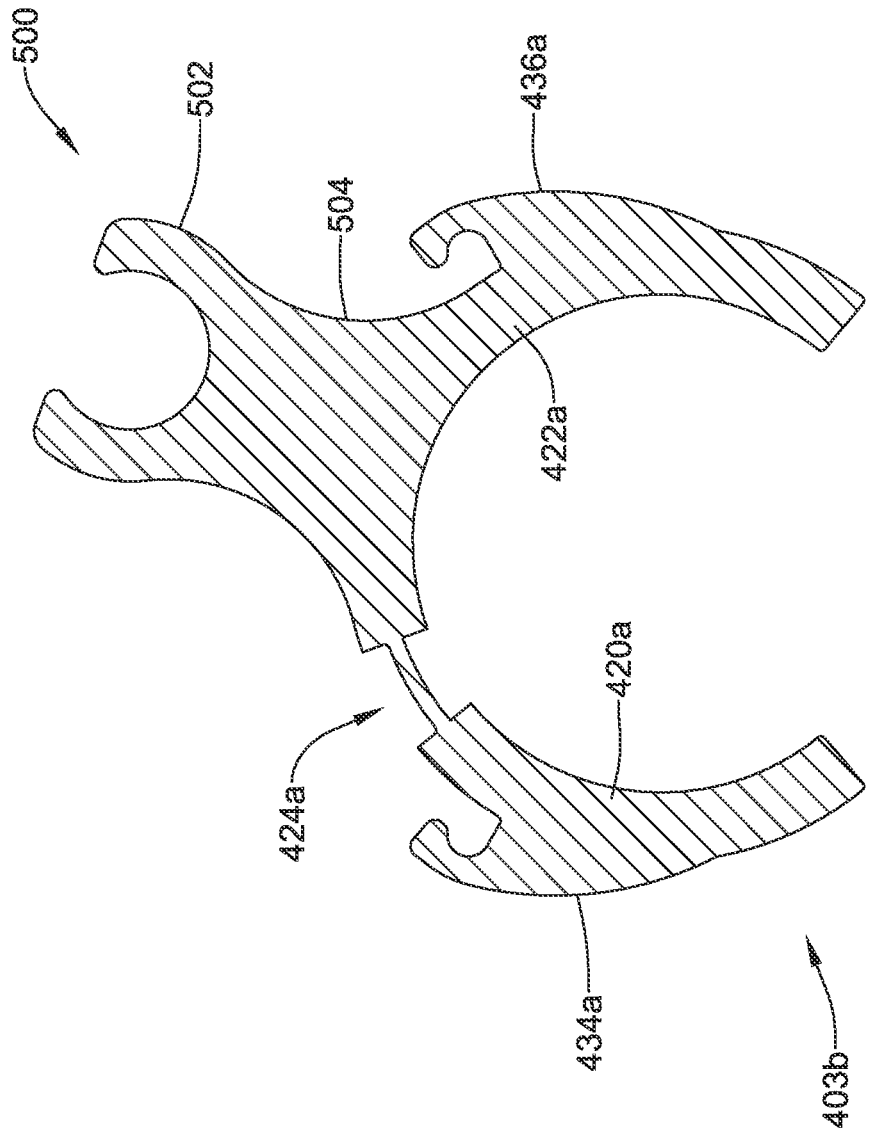
FIG. 33 is a cross-sectional view of the split ring attachment mechanism of FIG. 32, taken along line 33-33.

FIG. 32 is a perspective view of a split ring attachment mechanism 403b and FIG. 33 is a cross-sectional view of the split ring attachment mechanism 403b. The split ring attachment mechanism 403b includes an elongate body 409a that is divided into a first clamping portion 420a and a second clamping portion 422a by an elongate living hinge 424a. A hook 434a extends from the first clamping portion 420a and a corresponding hook 436a extends from the second clamping portion 422a. The split ring attachment mechanism 403b includes an elongate body 409a that defines the annular slot 413 as well as a pair of annular grooves 444a and 446a that are configured to accommodate an O-ring or other elastic member to secure the split ring attachment 403b in its locking configuration (as shown) by extending around the elongate body 409a from the hook 434a to the hook 436a.

It can be seen that the first clamping portion 420a is relatively smaller than the second clamping portion 422a, as the elongate living hinge 424a is offset relative to a position of the living hinge 424 as seen in FIG. 27 or FIG. 31, for example. In some embodiments, the first clamping portion 420a and the second clamping portion 422a may, in comparison to the first clamping portion 420 and the second clamping portion 422 (seen in FIGS. 27 and 31, for example) may not extend circumferentially about the endoscope as far as the first clamping portion 420 and the second clamping portion 422. In some embodiments, having the elongate living hinge 424a be offset better facilitates placing the first clamping portion 420a and the second clamping portion 422a about the endoscope or other delivery system. In some embodiments, offsetting the elongate living hinge 424a relative to the clip 500 means that the clip 500 does not potentially impact the flexibility of the elongate living hinge 424a.

The split ring attachment mechanism 403, 403a, 403b may be made of any suitable material. In some embodiments, the split ring attachment mechanism 403, 403a, 403b may be made of a polymer such as but not limited to PEEK (polyetheretherketone), ABS (acrylonitrile butadiene styrene), polycarbonate, rubber, silicone, thermoplastic elastomers such as but not limited to PEBA (polyether block amide), available under the PEBAX® name, SLA and others.

Figure 34:
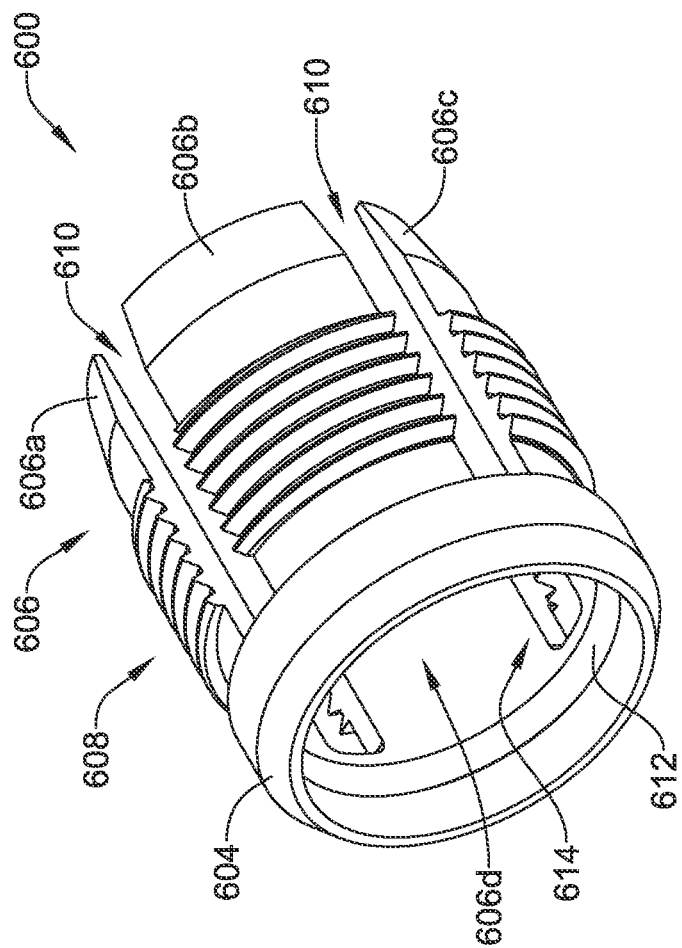
FIG. 34 is a perspective view of an inner collet member that may be used as part of an attachment mechanism in accordance with an example of the disclosure.
Figure 35:
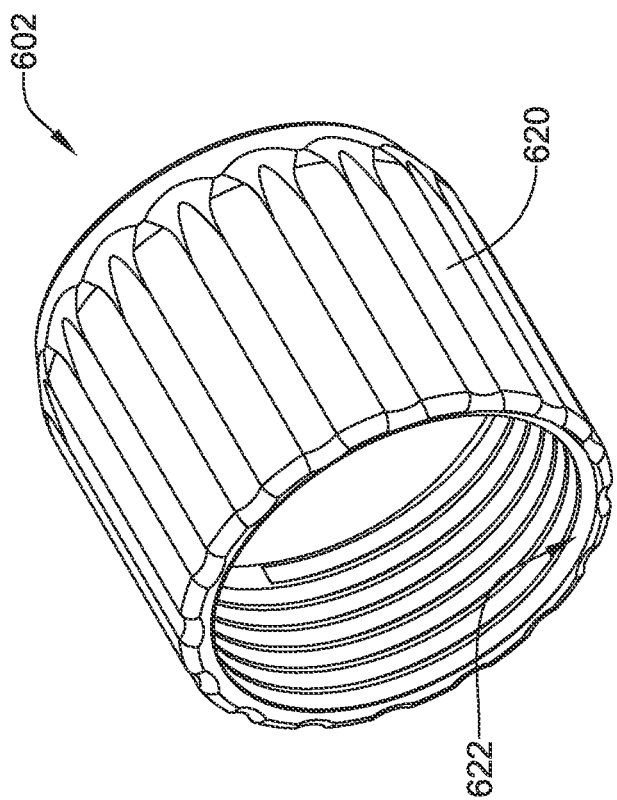
FIG. 35 is a perspective view of an outer collet member that may be used in combination with the inner collet member of FIG. 34 in accordance with an example of the disclosure.

FIGS. 25 through 33 illustrate a split ring attachment mechanism 403, 403a that may be used to releasably secure the distal endcap 14, 14a, 14b, 14c to the distal end of the endoscope 462. It will be appreciated that other attachment mechanisms may also be used. FIGS. 34 through 52 provide illustrative but non-limiting examples of attachment mechanisms that are disposable over an exterior of the endoscope 462 proximate a distal end thereof in order to releasably secure the distal endcap relative to the distal end of the endoscope 462. In some embodiments, for example, a suitable attachment mechanism may include an inner collet member 600 as shown in FIG. 34 that is configured to engage the distal endcap 14, 14a, 14b, 14c and form a compressive fit with the endoscope 462. A suitable attachment mechanism may also include an outer collet member 602 as shown in FIG. 35 that is configured to engage the inner collet member 600 in order to form the compressive fit between the inner collet member 600 and the endoscope 462.

As seen in FIG. 34, the inner collet member 600 includes an annular ring portion 604. In some embodiments, the annular ring 604 defines or otherwise includes an annular groove 612 that is configured to accommodate the fixation feature 401 present on the distal endcap 14, 14a, 14b, 14c. The fixation feature 401 is visible, for example, in FIG. 1. It will be appreciated that the interaction between the annular groove 612 and the fixation feature 401 may secure the inner collet member 600 to the distal endcap 14, 14a, 14b, 14c. The inner collet member 600 includes a number of fingers 606 that are adapted to interact with an outer surface of the endoscope 462 to provide a compressive fit between the inner collet member 600 and the endoscope 462. In some embodiments, the fingers 606 may be considered as extending axially from the annular ring 604 in a proximal direction. As illustrated, the inner collet member 600 includes a total of four fingers 606a, 606b, 606c and 606d. In some embodiments, the inner collet member 600 may have more than four fingers 606, or may have fewer than four fingers 606.

Figure 36:
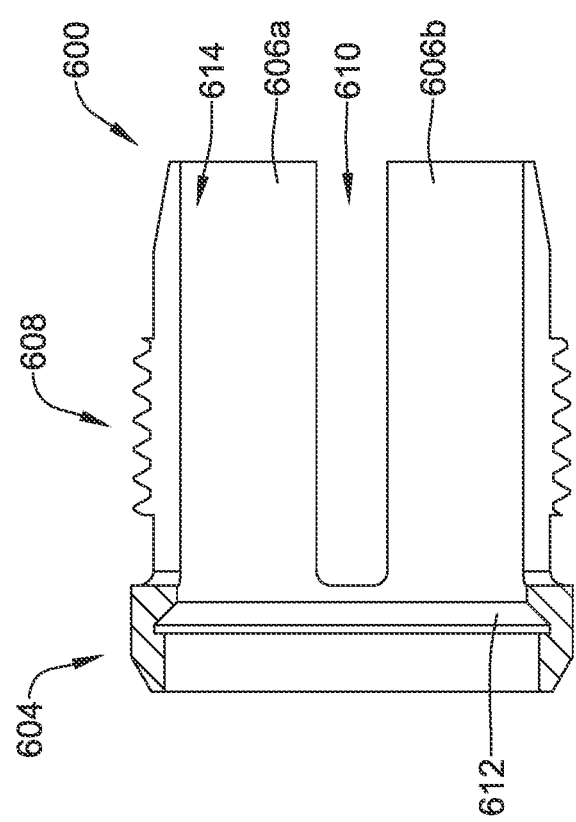
FIGS. 36 and 37 are schematic cross-sectional views of the inner collet member of FIG. 34 in accordance with an example of the disclosure.
Figure 37:
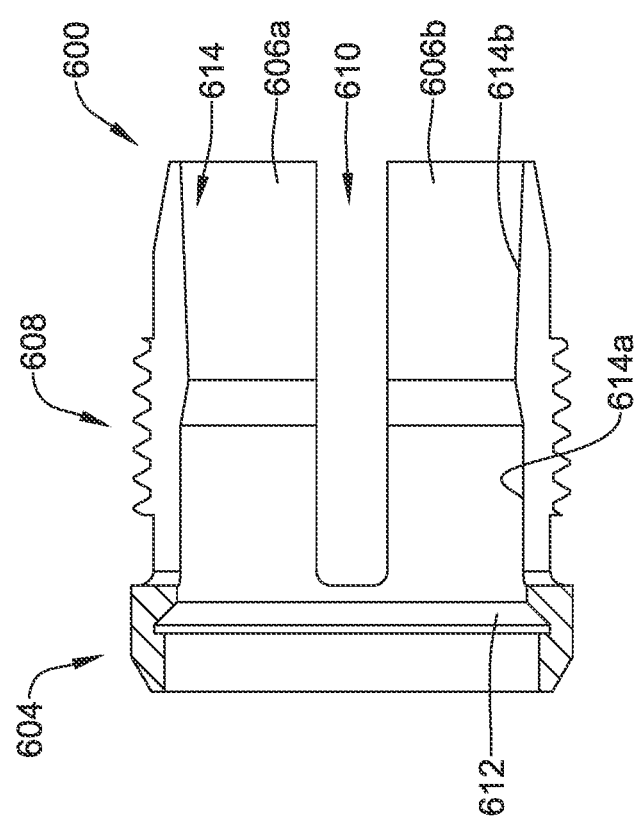

In some embodiments, as shown, the fingers 606 each include a threaded portion 608 that corresponds to threading on the outer collet member 602. The inner collet member 600 includes slots 610 disposed between adjacent fingers 606 such that the fingers 606 can bend inwardly as the outer collet member 602 is threaded over the inner collet member 600. It will be appreciated that the fingers 606 collectively define an inner surface 614 of the inner collet member 600. FIGS. 36 and 37 are schematic cross-sections of the inner collet member 600. In FIG. 36, the inner surface 614 may be seen as defining a constant diameter cylinder while in FIG. 37, the inner surface 614 is divided in to a first section 614a and a second section 614b, where the second section 614b defines a reduced-diameter cylinder relative to that defined by the first section 614a. In some embodiments, having a reduced-diameter portion helps with securing to a relatively smaller diameter endoscope 462, for example, and in some embodiments can lead to an increased surface contact area between the inner collet member 600 and the endoscope 462.

Figure 38:
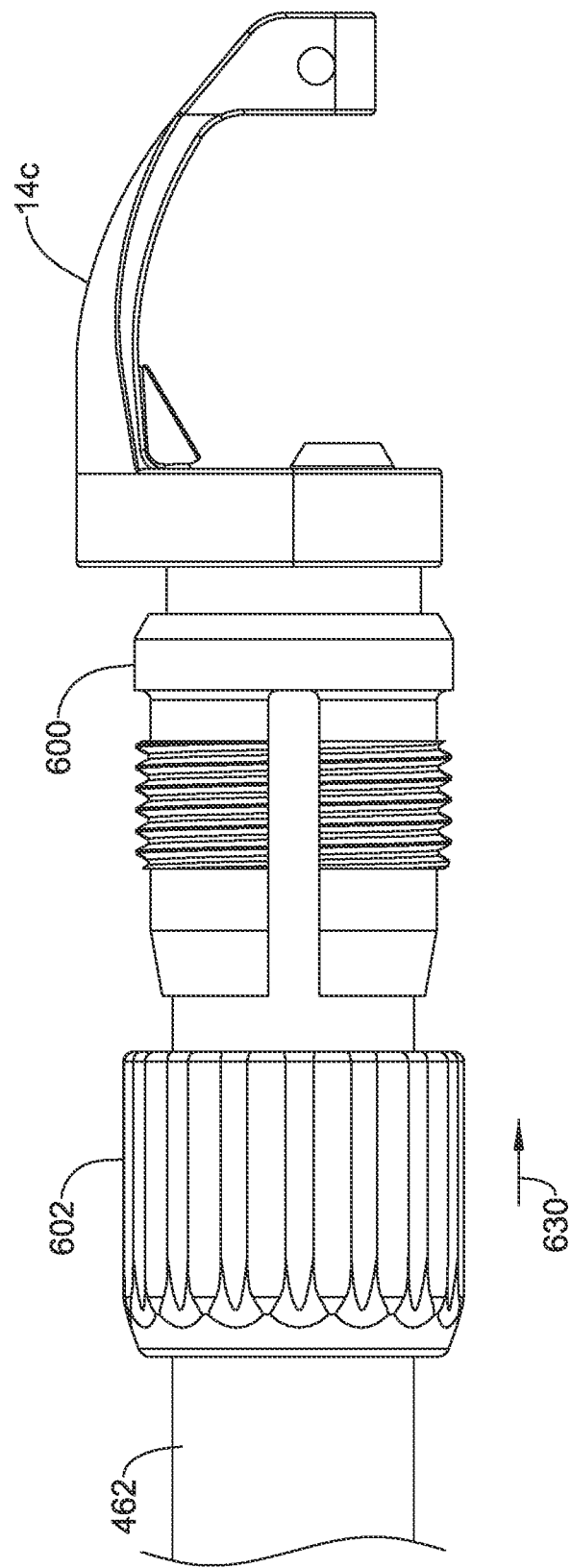
FIG. 38 is a side view of the inner collet member of FIG. 34 and the outer collet member of FIG. 35 positioned on an endoscope preparatory to securing a distal endcap to the endoscope in accordance with an example of the disclosure.
Figure 39:
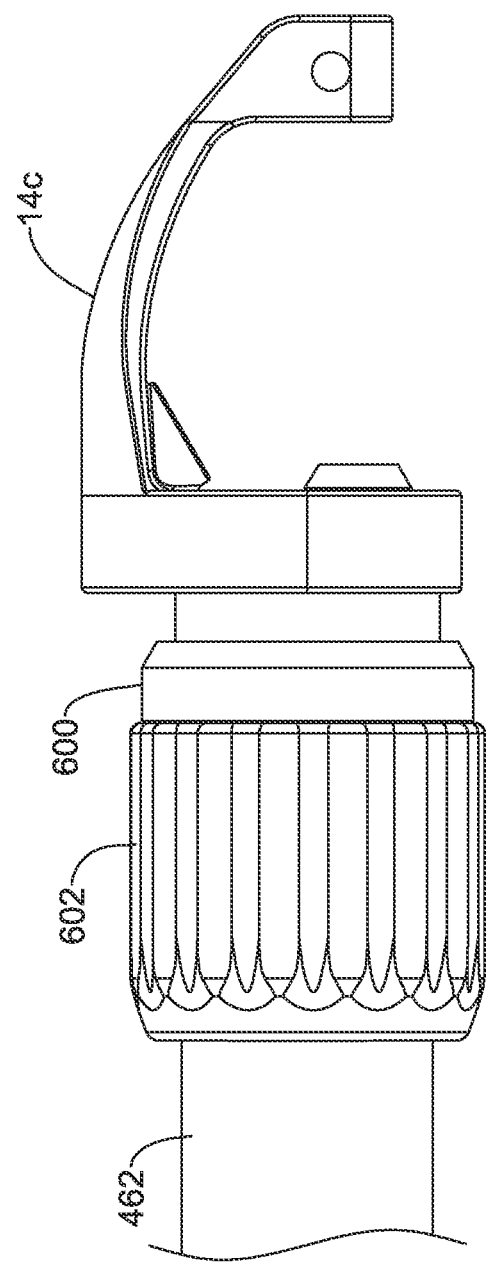
FIG. 39 is a side view of the inner collet member of FIG. 34 and the outer collet member of FIG. 35 in position having secured the distal endcap to the endoscope in accordance with an example of the disclosure.

Returning briefly to FIG. 35, the outer collet member 602 includes an outer knurled surface 620 that facilitates grasping and turning the outer collet member 602 relative to the inner collet member 600. The outer collet member 602 also includes a threaded inner surface 622 that engages the threaded portions 608 of each of the fingers 606 of the inner collet member 600. FIGS. 38 and 39 illustrate the inner collet member 600 and the outer collet member 602 in a detached and attached configuration, respectively, with an endoscope 462. The inner collet member 600 and the outer collet member 602 may secure a distal endcap such as the distal endcap 14c to the endoscope 462.

As can be seen in FIG. 38, the inner collet member 600 is positioned in engagement with the distal endcap 14c. While not visible, the fixation feature 401 may be engaged within the annular groove 612 to secure the inner collet member 600 to the distal endcap 14c. In some embodiments, the distal endcap 14 may be attachable to the endoscope 462 via the collet members 600, 602 by any configuration, e.g., tongue and groove, pins, and the like, so that the distal endcap 14 is secured to the endoscope 462 for performing a medical procedure. The outer collet member 602 is seen disposed over the endoscope 462. By moving the outer collet member 602 in a direction indicated by an arrow 630, the outer collet member 602 engages the inner collet member 600. Rotating the outer collet member 602 causes the outer collet member 602 to threadedly engage the inner collet member 600. As the outer collet member 602 continues to translate in the direction indicated by the arrow 630, the outer collet member 602 forces the fingers 606 into a compressive fit with the endoscope 462. FIG. 39 shows the distal endcap 14c secured to the endoscope 462 via the interaction between the inner collet member 600 and the outer collet member 602.

Figure 40:
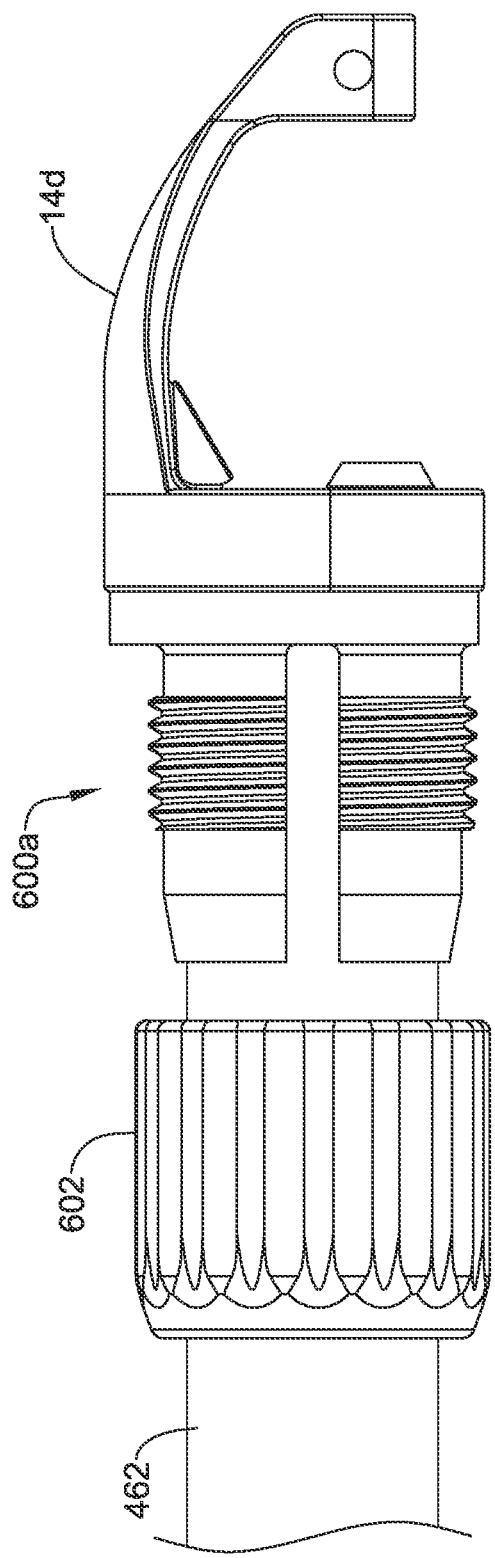
FIG. 40 is a side view of an attachment mechanism for securing a distal endcap to an endoscope in accordance with an example of the disclosure.

FIG. 40 shows an inner collet member 600a that is integrally formed with a distal endcap 14d. Operation is otherwise the same as that described with respect to FIGS. 38 and 39. In some embodiments, the inner collet member 600a may be integrally molded as part of the distal endcap 14d. In some instances, the inner collet member 600a may be adhesively secured to the distal endcap 14d. The inner collet member 600a may be separately formed, and then snap fit onto the distal endcap 14d. These are just examples.

Figure 41:
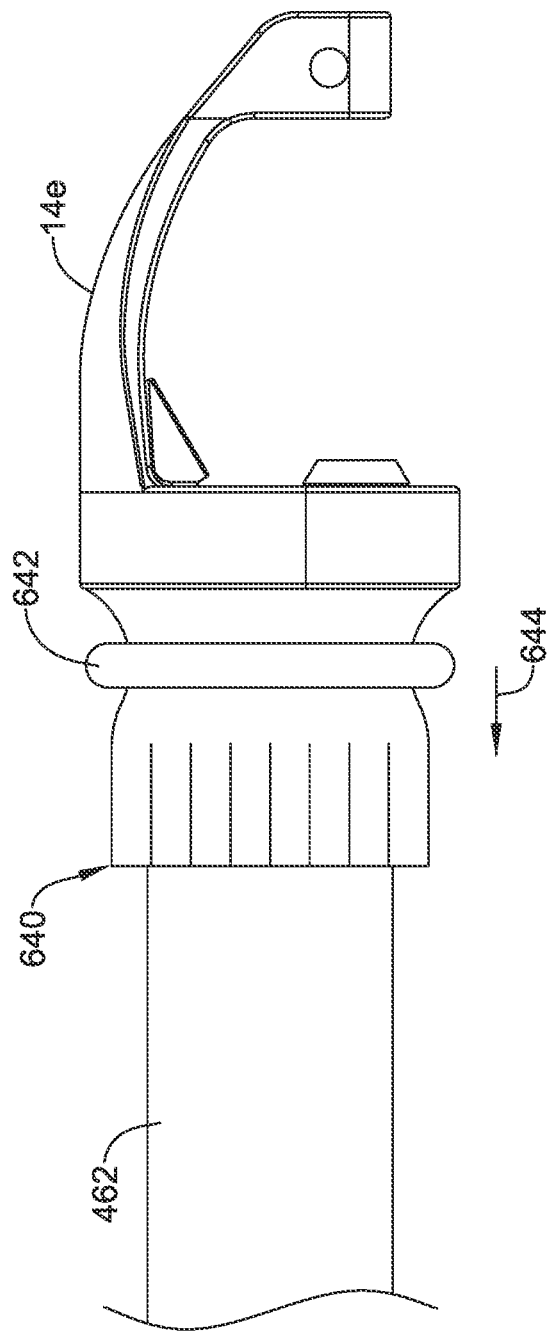
FIG. 41 is a side view of an attachment mechanism for securing a distal endcap to an endoscope in accordance with an example of the disclosure.
Figure 42:
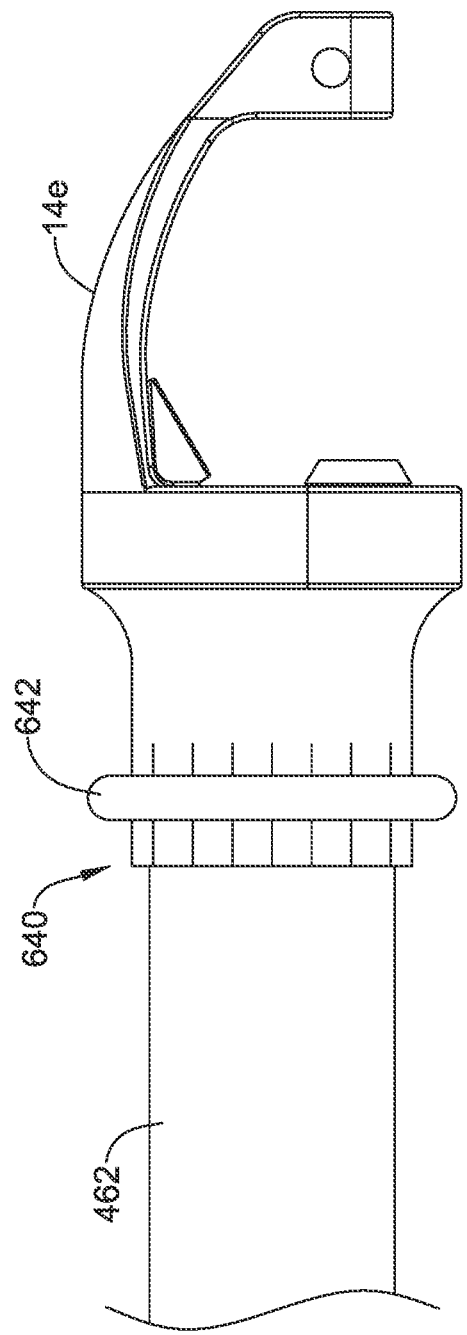
FIG. 42 shows the attachment mechanism of FIG. 41 having secured the distal endcap to the endoscope in accordance with an example of the disclosure.

FIGS. 41 and 42 show a distal endcap 14e that includes a number of proximally extending fingers 640. A ring 642 may be moved proximally, in a direction indicated by an arrow 644. As the ring 642 is moved proximally, the ring 642 compresses the proximally extending fingers 640 into a compressive fit with the endoscope 462. In some embodiments, the ring 642 may be a rigid ring. In some instances, the ring 642 may be elastomeric, and thus can stretch as the ring 642 is advanced proximally over the fingers 640, and thus can provide a compressive force on the fingers 640. FIG. 42 shows the distal endcap 14e secured to the endoscope 462.

Figure 43:
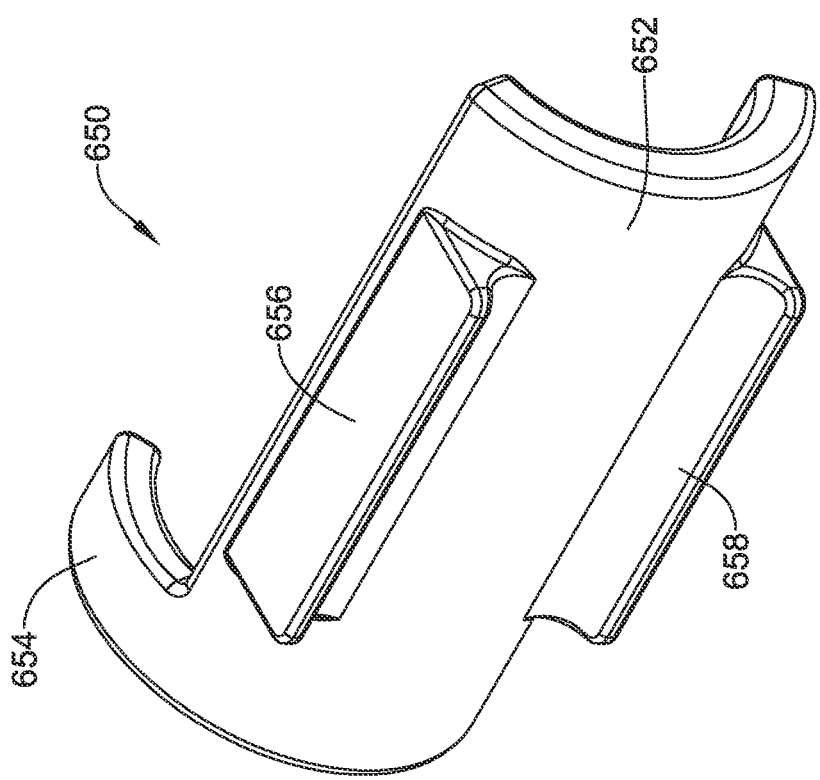
FIG. 43 is a perspective view of an attachment mechanism in accordance with an example of the disclosure.

FIG. 43 is a perspective view of an attachment mechanism 650 that in some ways is similar to the split ring attachment mechanism 403 described with respect to previous Figures. The attachment mechanism 650 includes a body 652 that is curved to fit part way around an endoscope such as the endoscope 462. The attachment mechanism 650 includes an annular ring portion 654 that extends radially around a greater distance than the body 652. While not visible, in some embodiments, the annular ring portion 654 includes a groove similar to the annular groove 612 that is configured to engage the fixation feature 401 of distal endcap 14, 14a, 14b, 14c. The attachment mechanism 650 includes hooks 656 and 658 extending radially outwardly from the body 652. The hooks 656 and 658 may accommodate an elastomeric member extending from the hook 656, around the endoscope 462 and to the hook 658.

Figure 44:
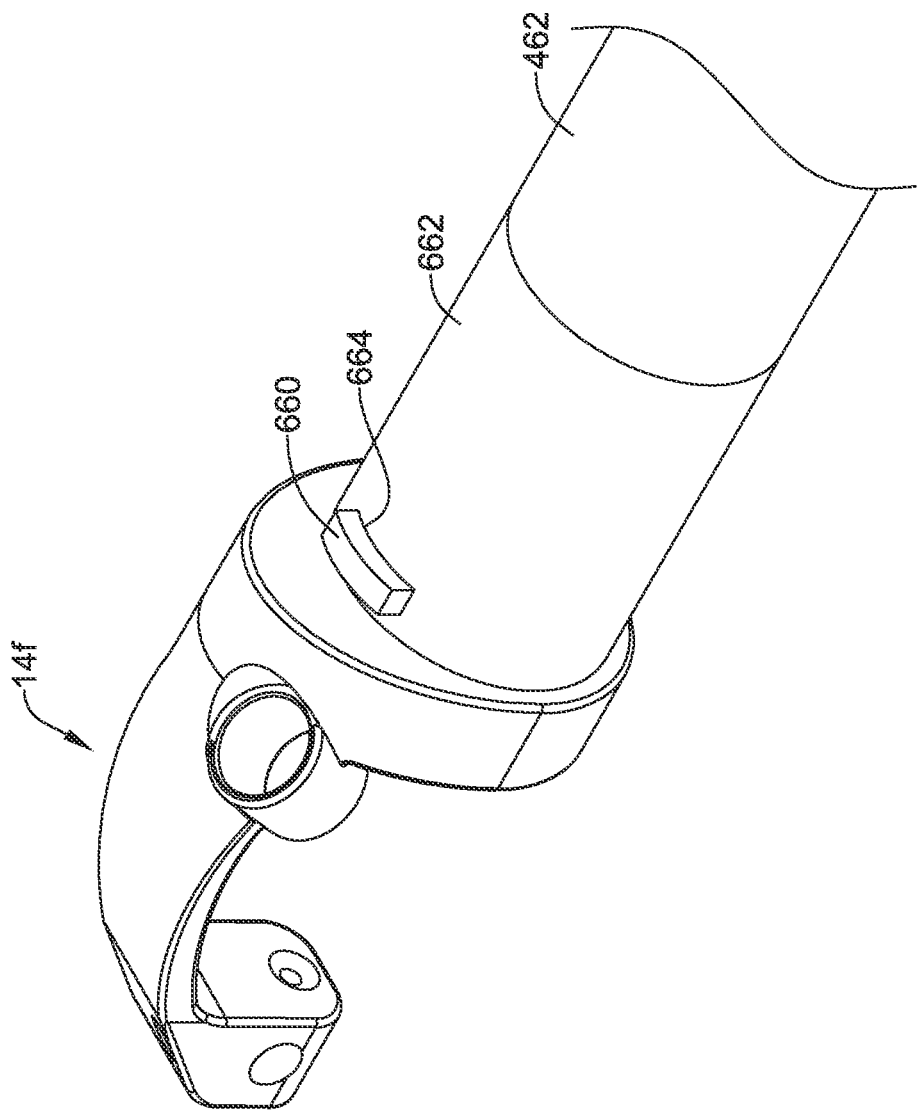
FIG. 44 is a perspective view of an attachment mechanism and distal endcap in accordance with an example of the disclosure.

FIG. 44 is a perspective view of a distal endcap 14f secured to the endoscope 462. The distal endcap 14f includes a fixation member 660 extending radially outwardly from the distal endcap 14f. The fixation member 660 may be integrally formed with the distal endcap 14f, for example, or may be adhesively secured to the distal endcap 14f. An elastomeric sleeve 662 may be configured to be stretched over the endoscope 462 to provide a compressive fit between the elastomeric sleeve 662 and the endoscope 462. In some embodiments, as shown, the elastomeric sleeve 662 includes a fixation aperture 664 that accommodates the fixation member 660 extending therethrough. It will be appreciated that the fixation member 660 and the fixation aperture 664 together provide an interference fit. While the fixation member 660 and the fixation aperture 664 are both illustrated as having a rectilinear shape, this is merely illustrative, as the fixation member 660 and the fixation aperture 664 may take any desired shape. In some embodiments, the distal endcap 14f may include two or more fixation members 660 and the elastomeric sleeve 662 may include two or more corresponding fixation apertures 664.

Figure 45:
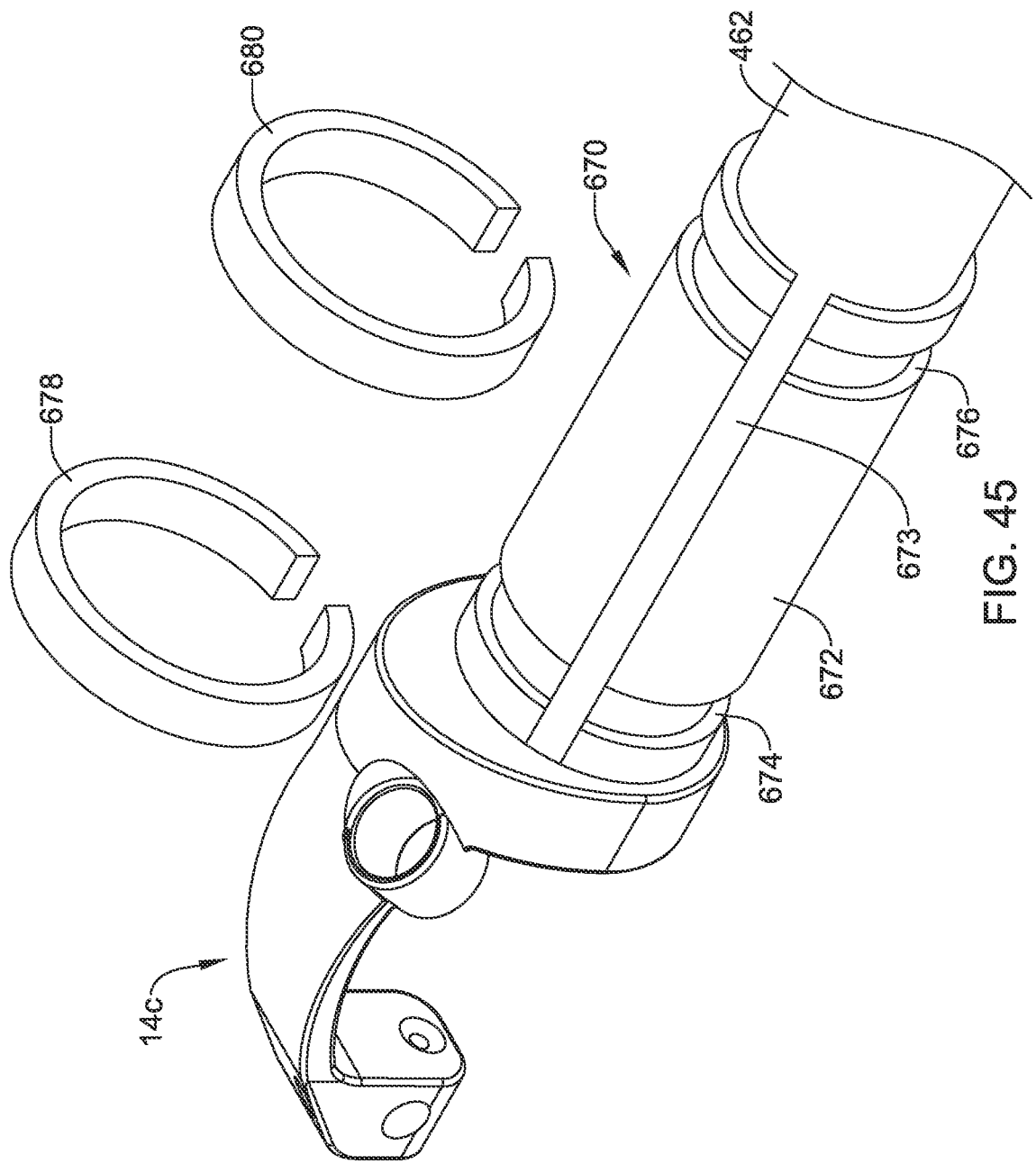
FIG. 45 is a perspective view of an attachment mechanism and distal endcap in accordance with an example of the disclosure.

FIG. 45 is a perspective view of an attachment mechanism 670 securing the distal endcap 14c to the endoscope 462. The attachment mechanism 670 is similar to the split ring attachment mechanism 403, 403a and includes a body 672. The body 672 defines annular grooves 674 and 676 for accepting snap rings 678 and 680, respectively. The snap rings 678, 680 are flexible enough to open sufficiently to fit over the body 672 and into the annular grooves 674, 676, respectively, and then reclose to provide a compressive force on the body 672 to close a gap 673 and thus provide a compressive fit between the attachment mechanism 670 and the endoscope 462. While not illustrated, the attachment mechanism 670 may have an interference fit with the endoscope 462.

Figure 46:
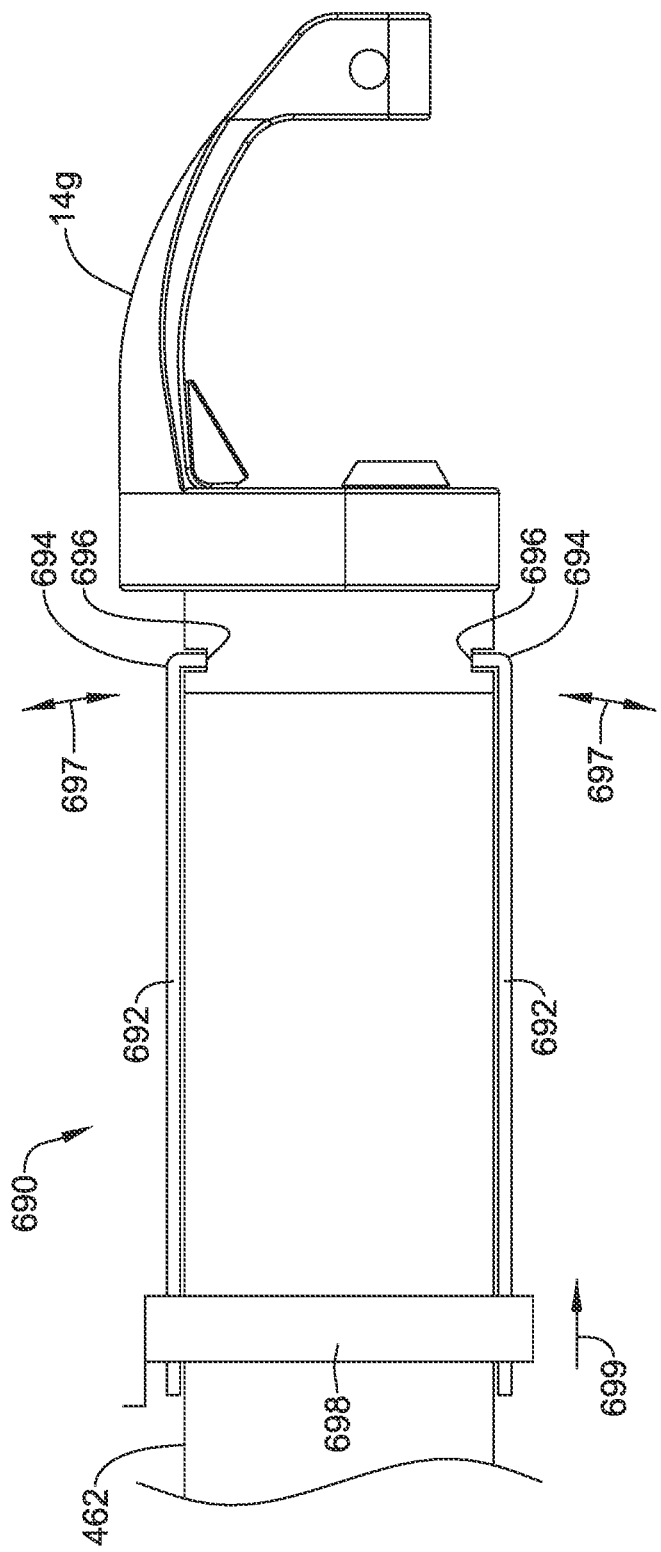
FIGS. 46 and 47 are side views of an attachment mechanism and distal endcap in accordance with an example of the disclosure.
Figure 47:
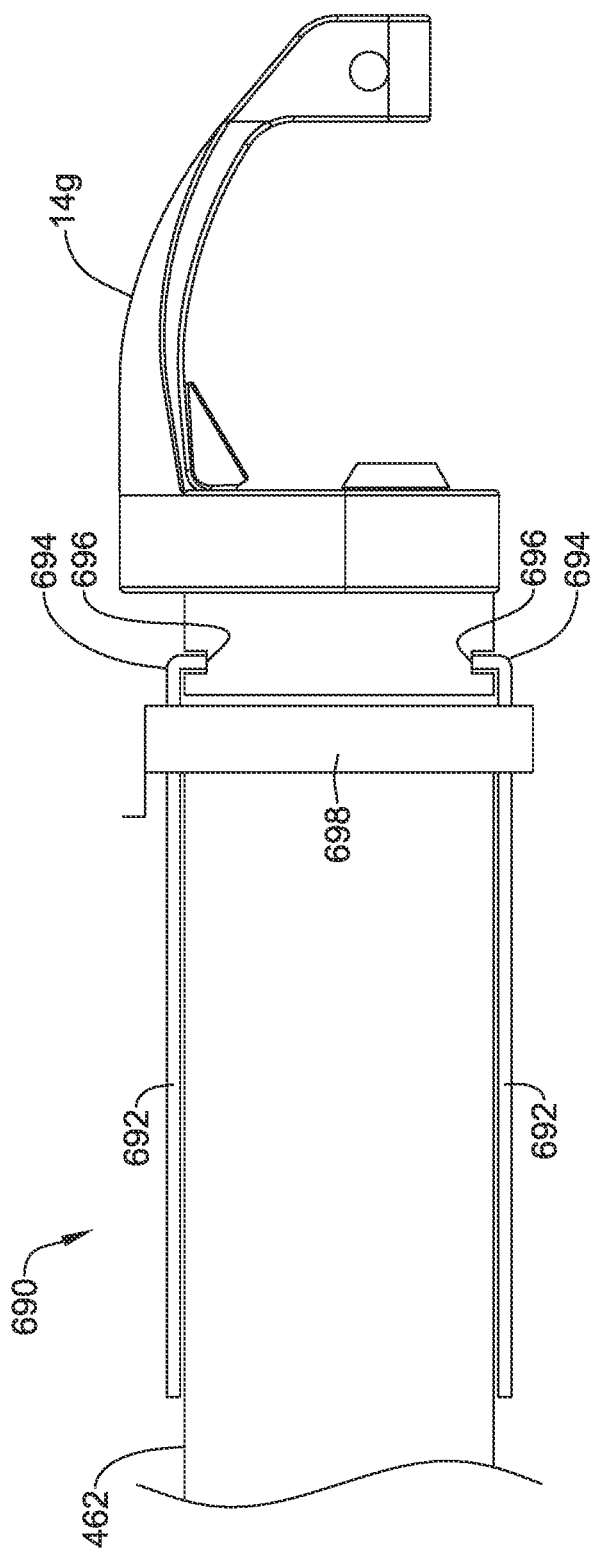

FIGS. 46 and 47 illustrate an attachment mechanism 690. The attachment mechanism 690 includes a number of hook members 692 that can be secured to the endoscope 462. Each of the hook members 692 includes a hook end 694 that is configured to fit into corresponding slots 696 that are formed in a distal endcap 14g. With a ring 698 positioned as shown in FIG. 46, the hook members 692 are free to rotate as indicated by arrows 697. As a result, the hook ends 694 can be inserted into the slots 696. By moving the ring 698 distally in a direction indicated by an arrow 699, the ring 698 prevents the hook ends 694 from backing out of the slots 696, thereby securing to the distal endcap 14g.

Figure 48:
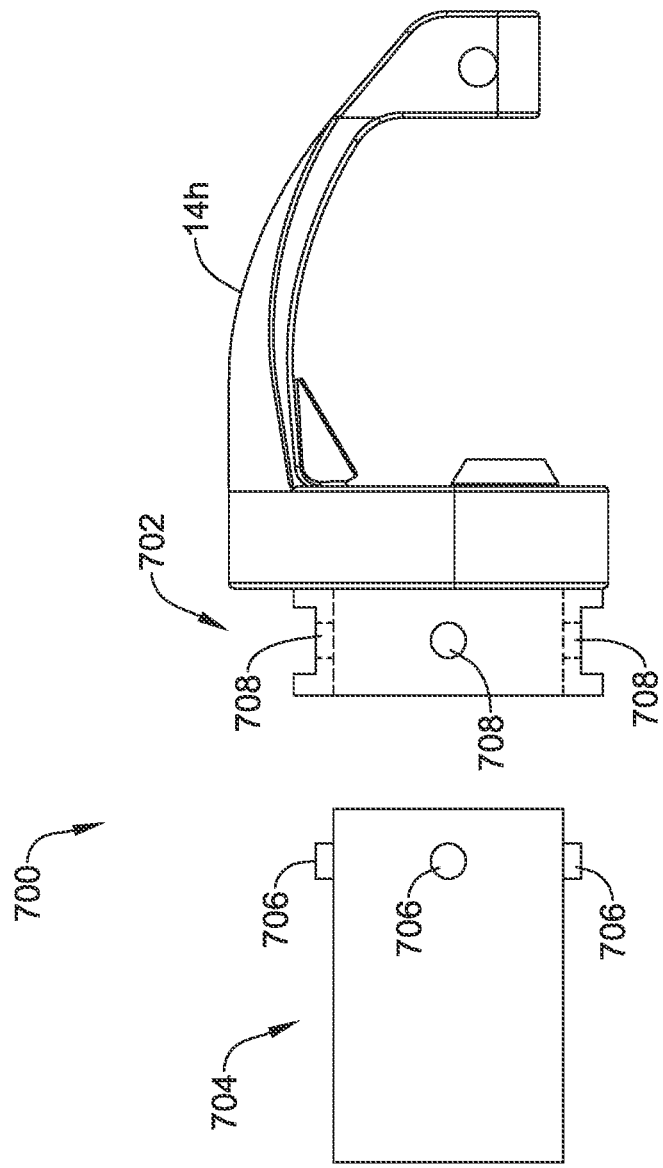
FIG. 48 is a side view of an attachment mechanism and distal endcap in accordance with an example of the disclosure.

FIG. 48 is a side view of an attachment mechanism 700 that includes a mounting feature 702 extending proximally from a distal endcap 14h and an adaptor 704 that is configured to be secured to the endoscope 462. The adaptor 704 includes radially extending pegs 706 that fit into corresponding holes 708 that are formed in the mounting feature 702. In some embodiments, this may be reversed, with the holes 708 formed in the adaptor 704 and the pegs 706 formed on the mounting feature 702.

Figure 49:
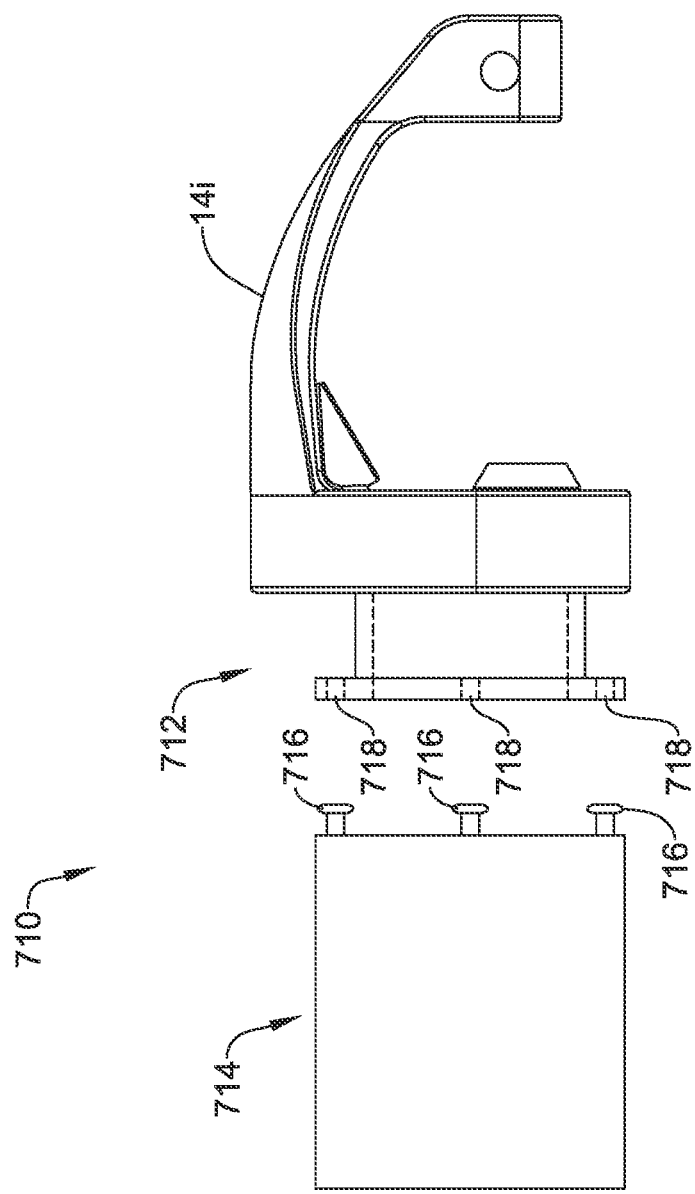
FIG. 49 is a side view of an attachment mechanism and distal endcap in accordance with an example of the disclosure.

FIG. 49 is a side view of an attachment mechanism 710 that includes a mounting feature 712 extending proximally from a distal endcap 14i and an adaptor 714 that is configured to be secured to the endoscope 462. The adaptor 714 includes axially extending pegs 716 that fit into corresponding holes 718 that are formed in the mounting feature 712. In some embodiments, this may be reversed, with the holes 718 formed in the adaptor 714 and the pegs 716 formed on the mounting feature 712.

Figure 50:
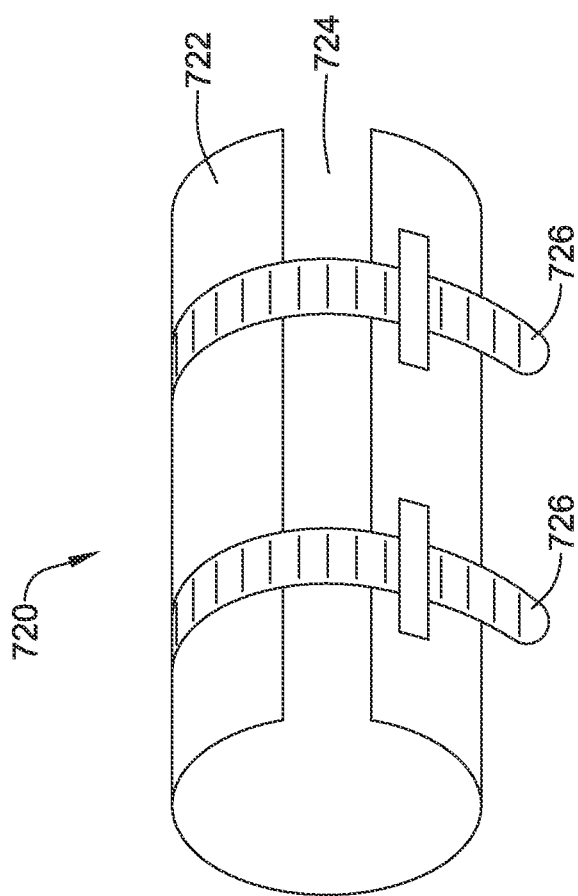
FIG. 50 is a side view of an attachment mechanism in accordance with an example of the disclosure.

FIG. 50 is a side view of an attachment mechanism 720 that may be used for securing a distal endcap to the endoscope 462. The attachment mechanism 720 has a body 722 that is configured to fit around the endoscope 462 and a distal endcap (not shown). As can be seen, the body 722 defines a slot 724 that facilitates placement of the attachment mechanism 720. Once placed, a pair of zip ties 726 may be used to compress the attachment mechanism 720 onto the endoscope, narrowing the slot 724.

Figure 51:
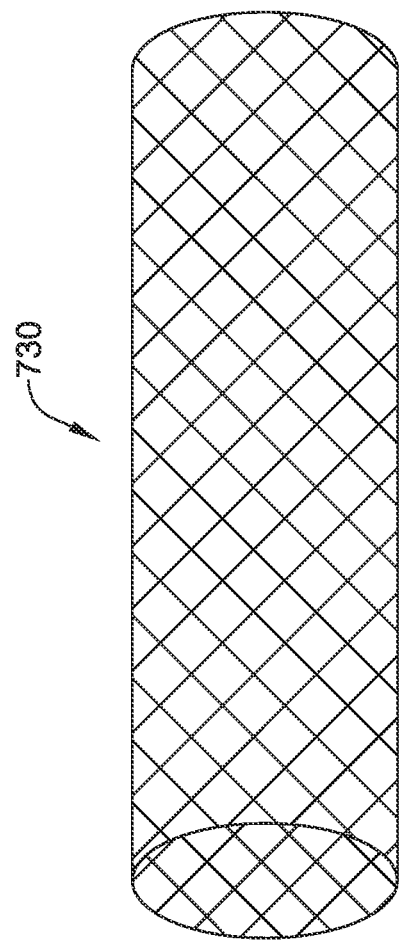
FIG. 51 is a side view of an attachment mechanism in accordance with an example of the disclosure.
Figure 52:
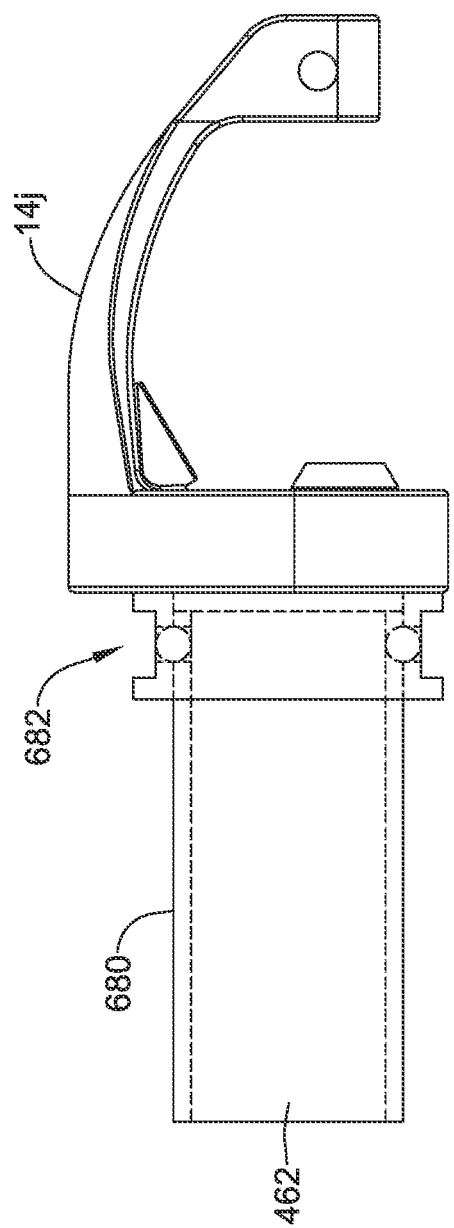
FIG. 52 is a side view of an attachment mechanism and distal endcap in accordance with an example of the disclosure.

FIG. 51 is a side view of an attachment mechanism 730 that may be used for securing a distal endcap to the endoscope 462. In simple terms, the attachment mechanism 730 may be considered as an example of a Chinese finger trap. The attachment mechanism 730 is a cylindrical, helically wound braid. Shortening the attachment mechanism 730 in an axial direction causes the attachment mechanism 730 to expand radially. In this configuration, the attachment mechanism 730 may be disposed over an endoscope and a distal endcap. Stretching the attachment mechanism 730 axially causes the attachment mechanism 730 to compress radially, which can secure the attachment mechanism 730 to both the endoscope 462 and the distal endcap. It will be appreciated that any further axial stretching, as would occur if the distal endcap moves away from the endoscope 462 during use, would further compress the attachment mechanism 462 radially.

FIG. 53 is a side view of a distal endcap 14j secured relative to the endoscope 462. The distal endcap 14j includes a fixation feature 682 that interacts with a sleeve 680 that is disposed over the endoscope 462. The sleeve 680 and the fixation feature 682 together provide a bearing ball quick-release feature similar to that used in connecting pressurized air hoses, for example.

It will be appreciated that a variety of different materials may be used in forming the devices described herein. In some embodiments, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An assembly for use in combination with an endoscope, the assembly comprising:
   a medical device having a proximal end adapted to be secured relative to a distal end of the endoscope, and a distal end; and
   an attachment mechanism having a proximal portion disposable over an exterior of the endoscope proximate the distal end thereof, and a distal portion the attachment mechanism configured to be releasably coupled with respect to the proximal end of the medical device to releasably secure the medical device relative to the distal end of the endoscope;
   wherein the attachment mechanism comprises:
      an inner collet member having a distal end that is configured to engage the proximal end of the medical device, with the distal end of the medical device extending distal to the distal end of the inner collet member, and a proximal end that is configured to be disposed over the exterior of the endoscope and to form a compressive fit with the endoscope; and
      an outer collet member that is configured to engage the inner collet member in order to form the compressive fit between the inner collet member and the endoscope.

2. The assembly of claim 1, wherein the outer collet member is threadedly engageable with the inner collet member.

3. The assembly of claim 1, wherein the medical device comprises an annular flange disposed at the proximal end of the medical device, and the inner collet member further comprises a corresponding annular slot disposed near a distal end of the inner collet member, the annular slot configured to engage the annular flange, thereby providing an interference fit between the medical device and the inner collet member.

4. The assembly of claim 3, wherein the inner collet member includes a body having a plurality of fingers extending axially in a proximal direction from the distal end of the inner collet member, the plurality of fingers defining an inner surface that is configured to engage the endoscope and an outer surface that provides threads to threadedly engage the outer collet adaptor.

5. The assembly of claim 4, wherein the outer collet member is configured to urge the plurality of fingers inwardly as the outer collet member is advanced over the inner collet member.

6. The assembly of claim 1, wherein the inner collet member is integrally formed with the medical device.

7. The assembly of claim 6, wherein the inner collet member comprises a plurality of fingers extending proximally from the medical device, and the outer collet member comprises a ring that is configured to be moved proximally over the plurality of fingers, thereby pressing the plurality of fingers into a compressive fit over the endoscope.

8. The assembly of claim 1, wherein the medical device comprises a suturing assembly that is adapted to transfer a needle back and forth through tissue, the needle carrying a suture.

9. An assembly for use in combination with an endoscope, the assembly comprising:
   a medical device having a proximal end configured to be releasably securable to a distal end of the endoscope, and a distal end;
   an inner collet member having a distal end with an interior surface that is configured to engage and be coupled with an exterior surface of the proximal end of the medical device, and a proximal end that is configured to engage and form a compressive fit with the endoscope; and
   an outer collet member that is configured to engage the inner collet member in order to form the compressive fit between the inner collet member and the endoscope.

10. The assembly of claim 9, wherein the outer collet member is threadedly engageable with the inner collet member in order to form the compressive fit with the endoscope with the distal end of the medical device extending distal to the distal end of the inner collet member.

11. The assembly of claim 9, wherein the medical device comprises an annular flange disposed at the proximal end of the medical device, and the inner collet member further comprises a corresponding annular slot disposed near a distal end of the inner collet member, the annular slot configured to engage the annular flange, thereby providing an interference fit between the medical device and the inner collet member.

12. The suture assembly of claim 9, wherein the inner collet member includes a body having a plurality of fingers extending axially in a proximal direction from the distal end of the inner collet member, the plurality of fingers defining an inner surface that is configured to engage the endoscope and an outer surface that provides threads to threadedly engage the outer collet member.

13. The assembly of claim 9, wherein the outer collet member is configured to urge the plurality of fingers inwardly as the outer collet member is advanced over the inner collet member.

14. The assembly of claim 9, wherein the medical device comprises:
   a translation assembly including:
      a needle configured to carry a suture;
      a distal shuttle configured to releasably secure the needle; and
      a sleeve disposable over the distal shuttle, the sleeve movable between a locked position in which the needle is secured to the distal shuttle and an unlocked position in which the needle is releasable from the distal shuttle; and
   a distal endcap securable to the distal end of the endoscope and configured to engage the needle when the needle is advanced distally into the endcap and to release the needle when the needle is locked to the distal shuttle and the distal shuttle is withdrawn proximally.

15. An assembly, comprising:
   an endoscope having a working channel and a distal end:
   a medical device having a proximal end configured to be releasably securable to the distal end of the endoscope, and a distal end;
   an inner collet member separate from the medical device and having a distal end that is configured to engage the medical device with the distal end of the medical device extending distal to the distal end of the inner collet member, and a proximal end that is configured to engage and form a compressive fit with the endoscope; and
   an outer collet member that is configured to engage the inner collet member in order to form the compressive fit between the inner collet member and the endoscope.

16. The assembly of claim 15, wherein the outer collet member is threadedly engageable with the inner collet member in order to form the compressive fit with the endoscope.

17. The assembly of claim 15, wherein the medical device comprises an annular flange disposed at the proximal end of the medical device, and the inner collet member further comprises a corresponding annular slot disposed near a distal end of the inner collet member, the annular slot configured to engage the annular flange, thereby providing an interference fit between the medical device and the inner collet member.

18. The suture assembly of claim 15, wherein the inner collet member includes a body having a plurality of fingers extending axially in a proximal direction from the distal end of the inner collet member, the plurality of fingers defining an inner surface that is configured to engage the endoscope and an outer surface that provides threads to threadedly engage the outer collet adaptor.

19. The assembly of claim 15, wherein the outer collet member is configured to urge the plurality of fingers inwardly as the outer collet member is advanced over the inner collet member.

20. The assembly of claim 15, wherein the medical device includes an element extending through the working channel of the endoscope.

\* \* \* \* \*